US009023619B2

(12) United States Patent
De Boer

(10) Patent No.: US 9,023,619 B2
(45) Date of Patent: May 5, 2015

(54) NON-NATURAL GELATIN-LIKE PROTEINS WITH ENHANCED FUNCTIONALITY

(75) Inventor: Arjo De Boer, Tilburg (NL)

(73) Assignee: Fujifilm Manufacturing Europe B.V. (NL)

( * ) Notice: Subject to any disclaimer, the term of this patent is extended or adjusted under 35 U.S.C. 154(b) by 0 days.

(21) Appl. No.: 13/881,407

(22) PCT Filed: Oct. 17, 2011

(86) PCT No.: PCT/GB2011/052002
§ 371 (c)(1),
(2), (4) Date: Apr. 25, 2013

(87) PCT Pub. No.: WO2012/056215
PCT Pub. Date: May 3, 2012

(65) Prior Publication Data
US 2013/0273603 A1    Oct. 17, 2013

(30) Foreign Application Priority Data

Oct. 26, 2010   (GB) .................................. 1018044.6

(51) Int. Cl.
*C07K 14/78*   (2006.01)
*A61K 38/00*   (2006.01)
*C07K 14/00*   (2006.01)
*A61K 38/39*   (2006.01)

(52) U.S. Cl.
CPC .............. *C07K 14/001* (2013.01); *A61K 38/00* (2013.01); *A61K 38/39* (2013.01); *C07K 14/78* (2013.01)

(58) Field of Classification Search
CPC ................................ C07K 14/78; A61K 38/00
USPC ........................ 530/356; 514/17.2; 435/69.1
See application file for complete search history.

(56) References Cited

U.S. PATENT DOCUMENTS

| 7,598,347 | B2 * | 10/2009 | Bouwstra et al. ............. 530/350 |
| 8,101,205 | B2 | 1/2012 | Bouwstra et al. |
| 8,158,756 | B2 | 4/2012 | De Boer et al. |
| 8,173,776 | B1 | 5/2012 | De Boer et al. |
| 8,198,047 | B2 | 6/2012 | De Boer et al. |
| 8,349,588 | B2 | 1/2013 | De Boer et al. |
| 8,349,589 | B2 | 1/2013 | De Boer et al. |
| 8,357,397 | B2 | 1/2013 | Bouwstra et al. |
| 2005/0229264 | A1 | 10/2005 | Chang et al. |
| 2006/0241032 | A1 | 10/2006 | Bouwstra et al. |
| 2010/0273215 | A1 | 10/2010 | Van Hautum et al. |
| 2011/0106243 | A1 | 5/2011 | Van Dongen et al. |
| 2011/0182960 | A1 | 7/2011 | Van Dongen et al. |
| 2011/0256222 | A1 | 10/2011 | De Boer et al. |
| 2012/0238502 | A1 | 9/2012 | Kluijtmans |
| 2013/0066049 | A1 | 3/2013 | Van Dongen |
| 2013/0157956 | A1 | 6/2013 | Kluijtmans et al. |

FOREIGN PATENT DOCUMENTS

| EP | 0926543 A1 | 6/1999 |
| EP | 1014176 A2 | 6/2000 |
| EP | 1238675 A1 | 11/2002 |
| EP | 2112997 A1 | 11/2009 |
| WO | 01/34646 A2 | 5/2001 |
| WO | 01/34801 A2 | 5/2001 |
| WO | 2008/103041 A1 | 8/2008 |

OTHER PUBLICATIONS

International Search Report and Written Opinion issued from corresponding PCT/GB2011/052002, dated Jan. 12, 2012.
Blodgett, James K., et al.,"Specific Cleavage of Peptides Containing an Aspartic Acid (β-Hydroxamic Acid) Residue," J. Am. Chem. Soc., 1985, pp. 4305-4313, vol. 107.
Fields, Gregg B., et al.,"Sequence Specificity of Human Skin Fibroblast Collagenase," The Journal of Biological Chemisty, 1987, pp. 6221-6226, vol. 262, No. 13, The American Society of Biological Chemists, Inc.
Fields, Gregg B.,"A Model for Interstitial Collagen Catabolism by Mammalian Collagenases," J. theor. Biol., 1991, pp. 585-602, vol. 153, Academic Press Limited.
Heinkoff, Steven, et al.,"Amino Acid Substitution Matrices from Protein Blocks," Proc. Natl. Acad. Sci., 1992, pp. 10915-10919, vol. 89.
Miller, Edward J., et al.,"Cleavage of Type II and III Collagens with Mammalian Collagenase: Site of Cleavage and Primary Structure at the NH2-Terminal Portion of the Smaller Fragment Released from Both Collagens" Biochemistry, 1976, pp. 787-792, vol. 15, No. 4.
Peng, Yong. Y., et al.,"Constructs for the expression of repeating triple-helical protein domains" Biomedical Materials, 2009, pp. 1-8, vol. 4.
Ramshaw, John A. M., et al.,"Gly-X-Y Tripeptide Frequencies in Collagen: A Context for Host-Guest Triple-Helical Peptides," Journal of Structural Biology, 1998, pp. 86-91, vol. 122, Academic Press.
Smith, T. F., et al.,"Identification of Common Molecular Subsequences," J. Mol. Biol. 1981, pp. 195-197, vol. 147.
Welgus, Howard G.,"The Gelatinolytic Activity of Human Skin Fibroblast Collagenase," The Journal of Biological Chemistry, 1982, pp. 11534-11539, vol. 257, No. 19.
Werten, Marc W. T., et al.,"High-yield Secretion of Recombinant Gelatins by *Pichia pastoris*," Yeast, 1999, pp. 1087-1096, vol. 15, John Wiley & Sons, Ltd.
Werten, Marc W. T.,"Secreted Production of a Custom-designed, Highly Hydrophilic Gelatin in *Pichia pastoris*," Protein Engineering, 2001, pp. 447-454, vol. 14, No. 6, Oxford University Press.

* cited by examiner

*Primary Examiner* — Karen Cochrane Carlson
(74) *Attorney, Agent, or Firm* — Banner & Witcoff, Ltd.

(57)   ABSTRACT

The invention concerns non-natural Gly-Xaa-Yaa-protein monomers and non-natural Gly-Xaa-Yaa-proteins comprising or consisting of multimers of the monomers. The non-natural Gly-Xaa-Yaa-proteins can be produced with enhanced monodispersity.

18 Claims, 1 Drawing Sheet

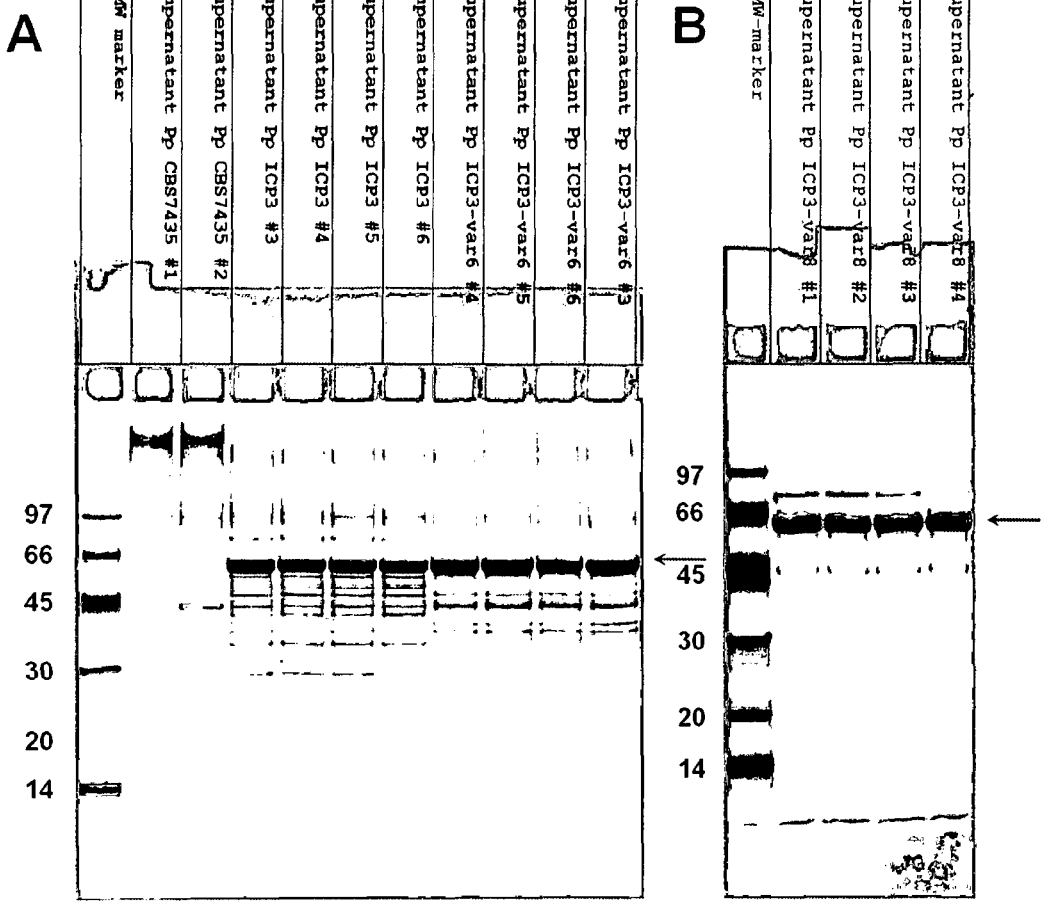

NON-NATURAL GELATIN-LIKE PROTEINS WITH ENHANCED FUNCTIONALITY

RELATED APPLICATION DATA

This application is a National Stage Application under 35 U.S.C. 371 of co-pending PCT application PCT/GB2011/052002 designating the United States and filed Oct. 17, 2011; which claims the benefit of GB patent application number 1018044.6 and filed Oct. 26, 2010 each of which are hereby incorporated by reference in their entireties.

FIELD OF THE INVENTION

The invention is in the field of recombinantly produced non-natural Gly-Xaa-Yaa-proteins, such as non-natural gelatins, and methods of their production. In particular the invention relates to non-natural Gly-Xaa-Yaa-proteins that can be produced in high yields. These non-natural Gly-Xaa-Yaa-proteins have improved resistance to certain proteases found in commonly used expression systems. The high stability towards proteases leads to improved yields and improved uniformity of the particular non-natural Gly-Xaa-Yaa protein.

BACKGROUND OF THE INVENTION

There is an increasing interest in recombinant Gly-Xaa-Yaa-proteins, (wherein Gly is glycine and Xaa and Yaa are independently any amino acid) such as gelatins. The widespread use and possibilities for use of these Gly-Xaa-Yaa proteins in medical and clinical applications means that economically viable production processes are required. This has prompted careful consideration of process variables and variations in protein sequences that could influence expression properties, and hence yields of the desired Gly-Xaa-Yaa-proteins.

Naturally occurring Gly-Xaa-Yaa-proteins such as gelatins, which are obtained by hydrolyzing collagen derived from animal tissues, are actually mixtures of a very large number of peptides and polypeptides. The molecular weight range of these (poly)peptides depends on the tissue from which the gelatin was derived and the processing conditions.

In principle, the recombinant production of Gly-Xaa-Yaa-proteins yields products in which all the component molecules have the same length (the same number of amino acid residues), since a particular gene typically encodes a single protein (barring genes that contain introns). The coding sequence of the gene determines the length of the nascent polypeptide. Secretory proteins also typically contain a signal sequence (signal peptide, preprotein sequence) that is removed during secretion. The remaining polypeptide is then considered to be the mature polypeptide.

Gly-Xaa-Yaa-proteins are sensitive to various proteases. Thus, Gly-Xaa-Yaa-proteins that are secreted by commonly used expression hosts such as *Pichia pastoris* or *Hansenula polymorpha* are heterogeneous in size due to (partial) digestion by intracellular and extracellular proteases.

In a strict interpretation only the mature full length polypeptide is considered to be the product. However in the field of repetitive biopolymers often both the mature polypeptide and its proteolytic fragments as considered the final product.

In the first interpretation, proteolysis can lead to a significant reduction in the yield of the product and the degradation products may pose a significant problem during purification of the mature protein (because of the similarity between the mature protein and its degradation products). The product in the sense of the second interpretation has some similarity to animal-derived gelatins: a product that comprises polypeptides with various lengths. However, the heterogeneity of this product can be disadvantageous in some applications.

Therefore, prevention of proteolysis will benefit both the yield and the quality of the product. Proteolysis can be avoided by inactivation of particular protease genes or by excluding target sites for these proteases in the product. Examples of both approaches can be found in the literature. EP926543 and Werten et al. 1999 (Yeast 15, 1087-1096) describe a production method of Gly-Xaa-Yaa proteins using the methylotrophic yeast *Pichia pastoris*, where the Gly-Xaa-Yaa proteins corresponding to fragments of the helical domains (consisting of Gly-Xaa-Yaa triplet repeats) of mouse type I collagen (encoding a 21 kDa and 28 kDa, calculated MW, COL1A1 peptide and a 53 kDa COL1A2) and rat type III collagen (COL3A1) are produced. A factor such as the fermentation pH was in certain cases found to influence the stability of the expressed product. The presence in the expressed sequence of target sites for certain proteases was also thought to be relevant.

In US 2006/0241032 XRGD-enriched gelatin-like proteins with a minimum (increased) level of XRGD motifs and with a certain distribution of said XRGD motifs are disclosed that were found to be highly suitable for cell adhesion and cell binding in medical and biotechnological applications. The cell binding peptides described therein have good cell attachment properties. However, susceptibility to degradation has been a limiting factor in the ability to produce large amounts of specific Gly-Xaa-Yaa-proteins. In EP2112997 XRGD-enriched gelatin proteins are disclosed that have an improved stability. This was achieved through avoidance of the use of particular amino acid residues (Asp, Pro, Hyp) as the X in the XRGD motifs in the sequence. However further improvement of the stability of recombinantly produced gelatin-like Gly-Xaa-Yaa proteins is desired.

The proteases in most expression systems are not known. Even less information is available on the targets of these proteases and their substrate specificity. Therefore, in most cases, sequences that are resistant to proteolytic attack must be determined empirically. In the current patent application we disclose new Gly-Xaa-Yaa-proteins that can be produced with improved yields and quality by the exclusion of proteolytic target sites that have not been previously identified

SUMMARY OF THE INVENTION

The present invention provides a non-natural Gly-Xaa-Yaa-protein having a molecular weight of at least 5 kDa, wherein at least 80% of the amino acids are present as Gly-Xaa-Yaa-triplets, wherein Gly is glycine and Xaa and Yaa are, independently, any amino acid, wherein said protein lacks the sequences GLA and GAA and has a calculated iso-electric point of at least 7.

Preferably the non-natural proteins essentially entirely consist of Gly-Xaa-Yaa-triplets. The sequences of these non-natural proteins are similar to naturally occurring gelatin which has a glycine residue as every third amino acid and a relatively large proportion of proline residues in the Xaa and Yaa positions, particularly in the Yaa position. The present inventors surprisingly found, that the proteins according to the present invention are secreted by microorganisms in high yields with low levels of accompanying proteolytic degradation products.

It is advantageous, for various end-use applications, to include an RGD motif in the non-natural Gly-Xaa-Yaa-proteins. The non-natural Gly-Xaa-Yaa-proteins according to the current invention are therefore preferably enriched in RGD sequences. Thus, in one embodiment the non-natural Gly-Xaa-Yaa-proteins comprise one or more RGD motifs. A definition of RGD-enriched is given below, however it is, for example, preferred for a gelatin with a length of about 300 amino acids, to comprise at least 2 RGD motifs, more preferably at least 3 RGD and especially at least 4 or more RGD motifs.

The inventors have surprisingly found that the recombinant non-natural Gly-Xaa-Yaa proteins of the present invention are more stable during recombinant production in certain microorganism and during the subsequent isolation and purification procedures. This results in a higher yield of the desired molecular species of the gelatin polypeptides with fewer accompanying fragments.

It has also been found that this monodispersity is further improved in non-natural Gly-Xaa-Yaa-proteins that have a calculated iso-electric point of at least 7, preferably at least 8, more preferably at least 9, and especially 10 or greater.

Preferably the non-natural Gly-Xaa-Yaa-proteins according to the present invention also have a low aspartic acid residue content apart from those residues which are present in the RGD motifs. Preferably the number percent of aspartic acid residues, apart from those residues which are present in the RGD motifs, is below 1.

It is also preferred that one or more RGD sequences in the recombinant non-natural Gly-Xaa-Yaa-proteins are not preceded by a proline (P) or hydroxyproline (O).

In one embodiment of the invention a non-natural Gly-Xaa-Yaa-protein is provided, comprising at least one XRGD motif per 5 kDa molecular weight of sequence, wherein X is any amino acid with the exception of D (Asp) and P (Pro) or O (hydroxyproline).

Preferably, X is selected from the group consisting of Y, W, F, C, M, K, L, I, R, H, V, A, G, N and E, especially E. Preferably each 5 kDa part of the non-natural Gly-Xaa-Yaa-protein comprises at least two XRGD motifs.

A high and stable expression level of non-natural Gly-Xaa-Yaa-protein sequences (and variants thereof and fragments of any of these) can be obtained in genetically engineered micro organisms. In selected micro organisms these proteins are secreted in high yields. Especially suitable microorganisms are methylotrophic yeasts, which are modified by the engineered nucleic acid sequences (DNA or RNA). These modified yeasts allow large scale fermentations for producing the artificial RGD comprising non-natural Gly-Xaa-Yaa-protein at high yields.

GENERAL DEFINITIONS

The non-natural Gly-Xaa-Yaa-proteins are polypeptides that comprise segments with consecutive Gly-Xaa-Yaa-triplets, where Gly is a glycine residue and Xaa and Yaa are independently any amino acid residue. The non-natural Gly-Xaa-Yaa-proteins can comprise components of sequences that can be found in nature. Gelatins constitute a well known class of Gly-Xaa-Yaa-proteins that are derived from animals, however, Gly-Xaa-Yaa-proteins can also be found in prokaryotes.

Whereas often the terms 'collagen', 'collagen-related', 'collagen-derived' or the like are also used in the art, the term 'gelatin' or 'gelatin-like' protein will be used throughout the rest of this description. Natural gelatin is a mixture of individual polymers with MW's ranging from 5,000 up to more than 400,000 daltons.

The terms "cell adhesion" and "cell attachment" are used interchangeably.

The terms "RGD sequence" and "RGD motif" and "Arg-Gly-Asp" are used interchangeably. The term "RGD-enriched" refers herein to amino acid sequences comprising at least one RGD motif. The term "RGD-enriched" in the context of this invention means that a certain level of RGD motifs, calculated as a percentage of the total number of amino acids per molecule is present and that there is a certain, more or less, even distribution of RGD sequences in the amino acid sequence. The level of RGD sequences can be expressed as a percentage. This percentage is calculated by dividing the number of RGD motifs by the total number of amino acids and multiplying the result with 100. Also, the number of RGD motifs is an integer starting from 1, 2, 3, . . . etc.

In particular "RGD-enriched" refers herein to amino acid sequences wherein the percentage of RGD motifs related to the total number of amino acids is at least 0.4 and if the amino acid sequence comprises 250 amino acids or more, each stretch of 250 amino acids contains at least one RGD motif. Preferably the percentage of RGD motifs is at least 0.6, more preferably at least 0.8, more preferably at least 1.0, more preferably at least 1.2, more preferably at least 1.5 and most preferably at least 1.8. Preferably "RGD-enriched" refers to polypeptides having at least one RGD sequence per 5 kDa of molecular weight. In the context of the present invention the molecular weight refers to the calculated molecular weight, in particular of the primary amino acid sequence, thus not taking into account possibly post-translational modifications of the particular host-micro-organisms wherein the present polypeptides were recombinantly produced. It is noted that of the preferred micro-organisms herein indicated, in particular yeasts, it is assumed no post-translational modifications of the Gly-Xaa-Yaa proteins occur. It is preferred that the present non-natural Gly-Xaa-Yaa proteins do not contain a part of 5 kDa without an RGD sequence.

A percentage of RGD motifs of more than at least 0.4 corresponds with more than at least 1 RGD sequence per 250 amino acids. The number of RGD motifs is an integer, thus to meet the feature of 0.4%, an amino acid sequence consisting of 251 amino acids should comprise at least 2 RGD sequences. Preferably the RGD-enriched GXY-proteins of the invention comprise at least 2 RGD sequences per 250 amino acids, more preferably at least 3 RGD sequences per 250 amino acids, most preferably at least 4 RGD sequences per 250 amino acids. In a further embodiment an RGD-enriched gelatin-like protein according to the invention comprises at least 4 RGD motifs per calculated molecular weight of 30 kD, preferably at least 6 RGD motifs per 30 kD.

"A relatively large proportion of proline residues in the Xaa and Yaa position" means that at least one third of the Gly-Xaa-Yaa triplets contains a proline residue.

A "fragment" is a part of a longer nucleic acid or polypeptide molecule.

"Native" or "natural" collagens or collagenous domains refer to those nucleic acid or amino acid sequences found in nature, e.g. in humans or other mammals.

"A non-natural polypeptide or protein" according to the present invention may have a certain degree of homology with polypeptide sequences of the same length which are part of natural molecules such as collagen. The recombinant non-natural Gly-Xaa-Yaa proteins as such however do not occur in nature.

The terms "protein" or "polypeptide" or "peptide" are used interchangeably and refer to molecules consisting of a chain of amino acids, without reference to a specific mode of action, size, 3-dimensional structure or origin. An isolated protein is a protein not found in its natural environment, such as a protein purified from a culture medium.

The term "support" or "cell attachment support" refers herein to any support which can be used to facilitate cell attachment and/or growth, such as culture dishes, microcarriers (e.g. microcarrier beads), stents, implants, plasters, etc.

The term "substantially identical", "substantial identity" or "essentially similar" or "essential similarity" means that two polypeptide, when aligned pairwise using the Smith-Waterman algorithm with default parameters, comprise at least 60%, 70%, 80% more preferably at least 85%, 90%, 95%, 96% or 97%, and particularly at least 98%, 99% or more amino acid sequence identity. Sequence alignments and scores for percentage sequence identity may be determined using computer programs, such as the GCG Wisconsin Package, Version 10.3, available from Accelrys Inc., 9685 Scranton Road, San Diego, Calif. 92121-3752, USA or using in EmbossWIN (e.g. version 2.10.0). For comparing sequence identity between two sequences, it is preferred that local alignment algorithms are used, such as the Smith Waterman algorithm (Smith T F, Waterman M S (1981) J. Mol. Biol. 147(1); 195-7), used e.g. in the EmbossWIN program "water". Default parameters are gap opening penalty 10.0 and gap extension penalty 0.5, using the Blosum62 substitution matrix for proteins (Henikoff & Henikoff, 1992, PNAS 89, 915-919).

The term "comprising" is to be interpreted as specifying the presence of the stated parts, steps or components, but does not exclude the presence of one or more additional parts, steps or components.

In addition, reference to an element by the indefinite article "a" or "an" does not exclude the possibility that more than one of the element is present, unless the context clearly requires that there be one and only one of the elements. The indefinite article "a" or "an" thus usually means "at least one".

"Monomer" refers to a polypeptide unit (or nucleic acid sequence encoding it) which can be used to generate a "multimer" (or "polymer", which is used interchangeably) by repeating the unit in a linear fashion to generate a longer polypeptide. The monomer units are preferably repeated without intervening amino acids, although optionally 1, 2, 3, 4, 5 or more linking amino acids may be present between monomer units.

The term "improved stability" means that a protein is not hydrolysed or is hydrolysed to a lesser extent, preferably by at least 10% or higher, under usual culture conditions of the yeast expression host and usual conditions under which the proteins are isolated compared to the corresponding sequences derived from natural occurring structures.

"Free of triple helix" structure refers to essentially the absence of the positive peak characteristic of the collagen triple helix in a circular dichroism spectrum. Circular dichroism spectrometry can be carried out as described in Werten et al. (2001, Protein Engineering 14:447-454).

DETAILED DESCRIPTION OF THE INVENTION

It was found, surprisingly, that it is possible to obtain high yields of improved, highly stable peptides or polypeptides. This is of great benefit to render the production process of Gly-Xaa-Yaa-proteins economically viable. The instant invention thus concerns non-natural Gly-Xaa-Yaa-proteins. The stability of the present proteins is beneficial for applications where gelatin has been used, in particular for applications that rely on the integrity of the gelatin/Gly-Xaa-Yaa-proteins. The polypeptides also do not display any health related risks, as they have a low antigenicity meaning that these polypeptides can be used with minimal risk of transferring pathological factors such as viruses, prions and the like. The present invention is directed to peptides, polypeptides or proteins, in particular to gelatins or gelatin-like proteins, which are highly suitable to be used in clinical, medical and/or biotechnological applications. For example the use as a plasma expander whereby intact molecules are kept in circulation is of interest and an application for which the present proteins are advantageously suited. Also, in particular, their uses in haemostats, dermal fillers and cell adhesion are areas of interest. In one embodiment the invention is directed to cell binding peptides or polypeptides that have improved properties compared to known Gly-Xaa-Yaa-RGD-comprising polypeptides, such as those described in US 2006/0241032, in particular the sequence designated as SEQ ID NO: 2 therein.

Although the non-natural proteins of the present invention are different from naturally occurring sequences they can display some homology to collagen. Thus, it is possible, that the non-natural protein sequence can exhibit more than 50% homology with a native collagen amino acid sequence. The majority of triads of amino acids in the Gly-Xaa-Yaa-proteins, preferably at least 80%, should have the sequence Gly-Xaa-Yaa, but an occasional deviating triad such as A-XaaYaa (A=alanine) does not alter the required properties. A substantial number of Gly-Xaa-Yaa-triplets should have the sequence Gly-Xaa-P or Gly-P-Yaa (wherein P is proline), Preferably more than half of the Gly-Xaa-Yaa triplets contains a proline residue. Preferably cysteine is avoided.

According to the invention recombinant gelatins are provided with excellent cell attachment properties and which demonstrate advantages such as improved stability, improved cell attachment and tissue support properties In one embodiment the non-natural Gly-Xaa-Yaa-protein has at least 60% sequence identity to SEQ ID NO:1. This sequence is also referred to herein as ICP-monomer.

In one embodiment the non-natural Gly-Xaa-Yaa-protein can also be defined as a protein comprising or consisting of an amino acid sequence having at least 70%, preferably at least 80%, and more preferably at least 90% or more amino acid sequence identity to SEQ ID NO: 1 or to a fragment thereof, more preferably at least 92%, 95%, 96%, 98%, 99% sequence identity or more. "Fragments" are parts of less than 1000 amino acids, such as 800, 600, 500, 300, 250, 200, 100, 50, 30 or less consecutive amino acids, but preferably at least 10, 15 or 20 amino acids.

In one embodiment the present invention provides non-natural recombinantly produced Gly-Xaa-Yaa:proteins which have a molecular weight of at least 5 kDa and which comprise at least one RGD sequence per 5 kDa of molecular weight. Preferably the non-natural Gly-Xaa-Yaa-protein has a calculated molecular weight of at least 15 kDa, preferably at least 20 kDa and more preferably at least 25 kDa.

Preferably each part of the non-natural Gly-Xaa-Yaa-protein of 5 kDa comprises at least one RGD sequence. Preferably the molecular weight is less than 200 kDa, more preferably less than 150 kDa. Such non-natural Gly-Xaa-Yaa-proteins were found to have an even further improved stability.

In order to obtain the present non-natural proteins, for example, nucleic acid sequences encoding natural gelatin sequences may be modified by site directed mutagenesis to give sequences having RGD motifs as defined herein. Of course it is also possible to simply design amino acid sequences comprising consecutive Gly-Xaa-Yaa-motifs, such as at least 5, 10, 15, 20, 30, 50, 100, 200, 300 or more consecutive Gly-Xaa-Yaa-motifs, whereby at least one, but preferably more RGD motifs are included in the sequence. Such designed polypeptides can be made by making nucleic acid sequences encoding these (using routine molecular biology techniques) and expressing these in a recombinant host cell. Preferably the spacing of the RGD-motifs is such that at least about 0, 10, 15, 20, 25, 30 or more intervening amino acids are present. When several RGD-motifs are present in the sequence, these can be spaced regularly or irregularly, depending on the application under consideration.

Preferably, the XRGD-motifs are part of the Gly-Xaa-Yaa-motifs, i.e. the sequence of Gly-Xaa-Yaa-triplets is not disrupted by the RGD-motif(s). For example in a sequence—GlyXaaYaa-GlyXaaYaa-GlyXaaR-GDYaa-GlyXaaYaa-GlyXaaYaa—the RGD-motif does not disrupt the consecutive Gly-Xaa-Yaa triplets.

Its also preferred that there is at least one XRGD motif (with X not being D or P or O) present in the non-natural Gly-Xaa-Yaa-protein. More preferably, more than 2 XRGD-motifs may be present in the non-natural Gly-Xaa-Yaa-protein, such as 3, 4, 5, 6 or more, wherein X is again any amino acid, except D, P or O.

In a further embodiment the invention relates to non-natural Gly-Xaa-Yaa-proteins which are not glycosylated. Glycosylation should be preferably prevented for applications where no immune response is desired. In a preferred embodiment, the non-natural non-natural Gly-Xaa-Yaa-proteins according to the invention are free of serine (Ser, S) and threonine (Thr, T) residues. It is believed that the absence of serine and threonine in the amino acid sequence may be an effective way to prevent the glycosylation in biotechnological production systems using, for instance, yeast cell cultures.

The non-natural Gly-Xaa-Yaa-protein monomer may comprise additional amino acids at one or both ends, e.g at the N- and/or C-terminal. For example, 1, 2, 3, 6, 9, 12, 15 or more amino acids may be present. These may be in the form of Gly-Xaa-Yaa-triplets. Additional amino acids at the termini, in particular the C-terminus, enhance the stability of the non-natural Gly-Xaa-Yaa-proteins, for example by preventing C-terminal degradation such as one by one cleavage of amino acids. Also additional amino acids at the termini facilitate multimer construction, the multimeric non-natural Gly-Xaa-Yaa-protein polypeptide may comprise N-terminal and C-terminal amino acids that are not part of the repeating amino acid sequence. In one embodiment the non-natural Gly-Xaa-Yaa-proteins according to the present invention, are preceded by a glycine-proline-proline (GPP) triplet and extended with two glycine residues (GG) at the carboxy-terminus.

The above described non-natural Gly-Xaa-Yaa-proteins according to this invention have a good stability to enzymatic and/or chemical proteolysis breakdown.

Preferably, with the non-natural Gly-Xaa-Yaa-proteins according to the present invention, no or reduced degradation or cleavage products, i.e. polypeptides of a smaller size than that of the encoded (full length) non-natural Gly-Xaa-Yaa-protein, are seen in/after a stability assay, e.g. on SDS-PAGE gels or by other methods such as LC-MS. Stability can for example be tested after the polypeptide is secreted into the culture medium of the yeast host, whereby the polypeptide is stable if substantially all (at least 95%, preferably at least 98%, 99% or most preferably 100%) of the recombinant polypeptide is full size. Stability to enzymatic or chemical hydrolysis can also be tested by incubating the polypeptide with one or more proteolytic enzymes or hydrolytic chemicals and by analyzing the resulting molecular weight after a specified period of treatment.

For example, when the molecular weight of recombinant natural gelatins and gelatins according to the invention produced in the same yeast host is compared after fermentation, the non-natural Gly-Xaa-Yaa-protein according to the invention is less degraded than the natural gelatin produced under the same conditions and in the same way. Degradation can also be quantified, e.g. by analyzing band intensities on SDS-PAGE gels loaded with the same amount of sample. See e.g. Werten et al. 1999 (supra).

Genes for non-natural Gly-Xaa-Yaa-proteins of the present invention can be derived from genes that encode natural collagenous sequences, with further modification to fulfill the amino acid sequence criteria described elsewhere herein. Alternatively, the genes for non-natural Gly-Xaa-Yaa proteins of the present invention can be synthesized de-novo. Gene synthesis is offered by various companies.

Gly-Xaa-Yaa-Protein Multimers

In a further embodiment multimers of the monomers described above are provided. Thus, the present invention encompasses a non-natural Gly-Xaa-Yaa-protein comprising or consisting of at least two repeats of the non-natural Gly-Xaa-Yaa-proteins as described above. Such multimers thus comprise or consist of at least 2, 3, 4, 5, 6, 7, 8, 9 or 10 repeats of the monomer sequence. Thus, a non-natural Gly-Xaa-Yaa-protein polypeptide is provided comprising or consisting of a multimer of a monomer sequence described above. Preferably, the monomer repeats are repeats of the same monomer unit sequence (repeats are identical in amino acid sequences), although optionally also combinations of different monomer units (having different amino acid sequences, each falling under the criteria above) may be used.

Preferably the monomer units are not separated by spacing amino acids, although short linking amino acids, such as 1, 2, 3, 4 or 5 amino acids, may be inserted between one or more of the monomers. Preferably there are less than 7 intervening amino acids between the monomer repeat units more preferably less than 3 amino acids.

In one embodiment the multimers comprise or consist of at least 2, 3, 4, 5, 6, 7, 8, 9 or 10 repeats of a monomer as described above. In one embodiment the multimers comprise or consist of at least 2, 3, 4, 5, 6, 7, 8, 9 or 10 repeats of a sequence having at least 60%, preferably at least 70%, 80%, 85%, 90%, 95%, 96%, 97%, 98%, 99% or more amino acid sequence identity or is substantially identical to SEQ ID NO: 1 or a fragment thereof (wherein the sequence similarity is determined as outlined above). Thus, non-natural Gly-Xaa-Yaa proteins include (SEQ ID NO: 1)$_n$ wherein n is an integer selected of 1 and higher, preferably n is 1 to 10 or more. Two repeats of the ICP monomer results in the dimer (SEQ ID NO: 2); four repeats of the ICP monomer results in the tetramer (SEQ ID NO: 3).

In one embodiment the multimer non-natural Gly-Xaa-Yaa-proteins according to the present invention, are preceded by a glycine-proline-proline (GPP) triplet and extended with two glycine residues (GG) at the carboxy-terminus. Thus, non-natural Gly-Xaa-Yaa-proteins according to the present invention include GPP((SEQ ID NO: 1))$_n$GG wherein n is an integer selected of 1 and higher, preferably n is 1 to 10 or more. For n=1 a gelatin according to the present invention called ICP (SEQ ID NO: 4) is obtained. In the above formula for n=2 the sequence ICP2 (SEQ ID NO: 5) is obtained; in above formula n=3 results in the sequence ICP3 (SEQ ID NO: 6); in above formula for n=4 the sequence ICP4 (SEQ ID NO: 7) is obtained.

Such multimers can be generated using known standard molecular biology methods.

Material and Compositions Comprising the Monomers and/or Multimers

The present invention is directed to peptides, polypeptides or proteins, in particular to non-natural Gly-Xaa-Yaa-proteins, which are suitable for cell adhesion and can be used in medical or biotechnological applications.

It was found that non-natural Gly-Xaa-Yaa-proteins according to the present invention are very suitable for coating cell culture supports which can be used in biotechnological processes or in medical applications.

RGD sequences in gelatins can adhere to specific receptors on the cell wall called integrins. These integrins differ in their specificity in recognising cell binding amino acid sequences. Although both natural gelatin and, for example, fibronectin may contain RGD sequences, gelatin can bind cells that will not bind to fibronectin and vice versa. Therefore fibronectin comprising RGD sequences cannot always replace gelatin for cell adhesion purposes.

Recombinantly produced gelatin does not suffer from the disadvantage of animal-derived gelatin, e.g. potential contamination with pathogens originating from the animal from which the gelatin was derived.

When used as, or in combination with, a cell culture support, the gelatin-like polypeptides according to the invention function as a cell binding polypeptide. It has the advantage over other polypeptides that it can also be metabolised by the cells growing on it.

A further advantage of recombinantly produced gelatins is that their molecular weight (MW) can be kept uniform. Natural gelatins, in particular gelatins isolated form natural sources, unavoidably have a broad molecular weight distribution with peptides smaller than 5 kDa up to large polymers with a molecular weight larger than 400 kDa. In particular in combination with microcarrier core beads as cell culture support, a disadvantage of smaller peptides is that they will adhere inside finer pores of the microcarrier which cannot be reached by the cells so that part of the added gelatin is not used. With recombinant production methods the gelatin can be designed with the desired molecular weight, preventing this undesirable effect.

A cell support comprising a non-natural Gly-Xaa-Yaa-protein according to the invention is provided. Such a cell support may be selected from the group consisting of
1) a cell-culture support, such as a core bead (e.g. a microcarrier bead) or a Petri dish or the like, coated with a coating comprising one or more non-natural Gly-Xaa-Yaa-proteins according to the invention;
2) an implant or transplant device (such as hip-, dental-, or other implants, stents, etc.) coated with a coating comprising one or more of the non-natural Gly-Xaa-Yaa-proteins according to the invention,
3) a scaffold or matrix for tissue engineering, such as artificial skin matrix material, coated with a coating comprising one or more non-natural Gly-Xaa-Yaa-proteins according to the invention;
4) a wound healing product coated with a coating comprising one or more non-natural Gly-Xaa-Yaa-proteins according to the invention;
5) a tissue adhesive comprising or consisting of one or more non-natural non-natural Gly-Xaa-Yaa-proteins according to the invention;

Preferably the cell support is selected from the group consisting of a non-natural Gly-Xaa-Yaa-protein coated implant or transplant material, a non-natural Gly-Xaa-Yaa-protein coated scaffold for tissue engineering, (part of) a dental product, (part of) a wound healing product, (part of) artificial skin matrix material and (part of) a tissue adhesive.

In one embodiment the cell supports provided herein preferably comprise only one non-natural Gly-Xaa-Yaa-protein according to the invention. The product is thus uniform in amino acid sequence, molecular weight, etc. Optionally the peptides may be cross-linked by, for example, chemical cross-linking.

In a different embodiment mixtures of polypeptides according to the invention may be used, such as 2, 3, 4, 5, or more different amino acid sequences according to the invention. The ratios of mixtures may vary, such as 1:1, or 10:1, 50:1, 100:1, 1:100, 1:50, 1:10, and ratios in between. Optionally these mixtures of proteins, or parts thereof, may also be crosslinked.

When using the non-natural Gly-Xaa-Yaa-protein monomer(s) and/or multimers for coating porous microcarrier beads, preferably polypeptides with a molecular weight of at least about 30 kDa are used, more preferably at least about, 40 kDa, especially at least about 50 kDa, more especially at least about 60 kDa and particularly at least about 70 kDa or more. The reason for this is that smaller polypeptides may enter the pores on the beads, thereby not contributing to the cell attachment properties of the coated beads. Thus, the coating process may be inefficient, especially if low concentrations of protein are used to coat the beads.

Preferably the molecular weight of the non-natural Gly-Xaa-Yaa or gelatin-like protein used is uniform, with more than 75%, preferably more than 85%, more preferably more than 95% and especially at least 98% of the protein having a uniform MW within 20% from the selected molecular weight.

By selecting a molecular weight, within the above specified range, in a coating process the viscosity of the non-natural Gly-Xaa-Yaa or gelatin-like protein coating solution can be accurately controlled. Complete or, more important, partial gelling of such a gelatin solution can be prevented while being able to select a high as possible concentration of the gelatin. The uniform gelatin ensures a process of identically coated microcarriers. The uniform coating process allows the use of a minimum amount of gelatin and the use of a minimum volume of gelatin coating solution. This results in a more efficient coating process than those known in the art.

In one embodiment of the invention non-porous core beads are coated with gelatin of the invention. Suitably non-porous core beads are made of polystyrene or glass. Other suitable non-porous materials are known to those skilled in the art.

A particular advantageous embodiment of the invention is a process wherein porous core beads, such as beads from modified dextran or cross-linked cellulose, or (porous) polystyrene, in particular DEAE-dextran, are coated with the non-natural Gly-Xaa-Yaa-protein of the invention. Other suitable porous materials are known to those skilled in the art, and include, for example, other chemically modified or non-modified polysaccharides.

The size of the beads may vary from 50 µm to 500 µm. Typical mean microcarrier bead sizes are about 100 µm, about 150 µm or about 200 µm in physiological saline. Size ranges with at least 90% of the beads lying within the range may vary from 80 to 120 µm, 100 to 150 µm, 125 to 175 µm or 150 to 200 µm.

A wide range of cells may be cultured on microcarriers. For instance, cells from invertebrates, from fish, birds and cells of mammalian origin may all be cultivated. Transformed and normal cell lines, fibroblastic and epithelial cells and even genetically engineered cells may also be cultivated on microcarriers for various biological applications such as for the production of immunologicals like interferons, interleukins, growth factors etc. Cells cultured on microcarriers also serve as hosts for a variety of viruses that are used as vaccines like foot and mouth disease or rabies.

Microcarrier cultures have a wide number of applications other than mass cultivation. Cells growing on microcarriers serve as an excellent tool for studying different aspects of cell biology such as cell-to-cell or cell-to-substratum interactions. Cell differentiation and maturation, metabolic studies may also be carried out using microcarriers. Such cells can also be used for electron microscopic studies or for the isolation of cell organelles such as the cell membrane. Also, this system is essentially a three-dimensional system and serves as a good 3-D model. Similarly, co-cultivation of cells can be done using this system. Thus applications include the production of large quantities of cells, viruses and cell products (e.g. interferon, enzymes, nucleic acids, hormones), studies on cell adhesion, differentiation and cell function, perfusion column culture systems, microscopy studies, harvesting mitotic cells, isolation of cells, membrane studies, storage and transport of cells, assays involving cell transfer and studies on uptake of labeled compounds.

Microcarriers may also be used for the depletion of macrophages from a population of spleen cells. DEAE-dextran microcarriers coated with the recombinant non-natural Gly-Xaa-Yaa proteins of this invention can potentiate stimulation of lymphocytes by concanavalin A (con A). Microcarrier beads confluent with allogenic tumour cells can be injected in mice to increase humoral and cell-mediated immunity. Plant protoplasts can be immobilised on DEAE-dextran microcarriers coated with the non-natural Gly-Xaa-Yaa-proteins of this invention.

As a result of the large surface area to volume ratio provided by microcarriers, they can successfully be used for a variety of biological productions on a laboratory scale as well as an industrial scale of for instance even 4000 litres or more.

Large scale production of expressed products can be accomplished with gelatin-coated microcarriers. Loading of microcarriers in production scale bioreactors is generally 20 g/l, but may be increased up to 40 g/l. Microcarriers may be used in batch and perfusion systems, in stirred cultures, and wave bioreactors, as well as to increase the surface area of traditional stationary monolayers and roller cultures.

In a further preferred embodiment the non-natural Gly-Xaa-Yaa-protein is in essence free of hydroxyproline residues. Hydroxylation of proline is a requirement for the formation of triple helices in collagen and plays a role in gelation of gelatin. In particular less than 10%, preferable less than 5% more preferably less than 3% and especially less than 1% of the amino acid residues of the non-natural Gly-Xaa-Yaa-proteins are hydroxyprolines. Most preferably the protein is free from hydroxyprolines. In applications where the gelling capability of the non-natural Gly-Xaa-Yaa-protein is unfavorable the hydroxyproline-free proteins can be used in higher concentrations, and the solutions will be less viscous requiring less vigorous agitation, resulting in less shear forces on the cultured cells. As described in WO 02/070000 A1, non-natural Gly-Xaa-Yaa-proteins which are in essence free from hydroxyprolines do not show immune reactions involving IgE in contrast to natural gelatin. Absence of hydroxyprolines can for example be achieved by expression in *Pichia* hosts, such as *Pichia pastoris*, which has not been transformed or does not comprise a functional prolyl-4-hydroxlase enzyme.

The amount of hydroxyprolines can be determined by any standard amino acid analysis method like, for example, described in HP AminoQuant Series II, operators handbook, 1990, Hewlett-Packard GmbH, Federal Republic of Germany, Waldbronn Analytical Division, HP Part No. 01090-90025.

In one embodiment the present non-natural Gly-Xaa-Yaa-proteins are free of triple helix structure.

In a further embodiment the invention relates to the use of non-natural Gly-Xaa-Yaa-proteins according to the invention to block surface receptors on cells and to make compositions for blocking such receptors. Blocking of receptors of cells is applied in for example inhibiting angiogenesis or in blocking integrins on cardiac fibroblasts.

Cell supports coated with non-natural Gly-Xaa-Yaa-protein according to the invention, on which cells have been grown can be applied during, for example, transplantation of skin or wound treatment or to enhance bone or cartilage (re)growth. It is also possible to coat implant materials with non-natural Gly-Xaa-Yaa-proteins of the invention to adhere cells and so promote implantation.

In one embodiment the present inventions concerns a composition comprising a non-natural Gly-Xaa-Yaa-protein according to the present invention. The composition may be a pharmaceutical composition or a nutritional- or nutraceutical composition. For example the present non-natural Gly-Xaa-Yaa-proteins, in particular the multimers, can be used as a plasma expander in blood substitute liquids.

In yet another embodiment of the invention a controlled release composition comprising a non-natural Gly-Xaa-Yaa-protein is provided. The composition may, thus further comprise one or more drugs. Controlled release formulations can be made as known in the art, for example by using the non-natural Gly-Xaa-Yaa-proteins or compositions comprising these as a coating layer surrounding one or more drugs or for making a matrix in which the drug is enclosed or incorporated. The controlled release composition can be administered by injection (subcutaneous, intravenous or intramuscular) or orally or via inhalation. The controlled release composition can also be implanted via surgery. Yet another suitable route of administering is via an external wound dressing or even transdermally.

The controlled release composition preferably comprises the non-natural Gly-Xaa-Yaa-protein in a cross-linked form, e.g. chemically crosslinked. The invention further provides use of a controlled release composition as described herein for use in the treatment of pain, cancer therapy, cardiovascular diseases, myocardial repair, angiogenesis, bone repair and regeneration, wound treatment, neural stimulation/therapy and diabetics.

Another embodiment of the invention provides a hemostat composition comprising a non-natural Gly-Xaa-Yaa-protein as described above. For use as a hemostat the non-natural Gly-Xaa-Yaa-protein of this invention is preferably transferred into a sponge like material using techniques known in the art. The sponge can be impregnated with suitable anti bleeding compounds. Furthermore the non-natural Gly-Xaa-Yaa-protein sponge can be combined with other sponge like material or the sponge can be made by evaporation of an aqueous solution of the non-natural Gly-Xaa-Yaa-protein of this invention in which the solution can comprise other components to improve sponge properties, like adhesion to the wound, blood take up capacity and the like. Suitable compounds to combine with the recombinant non-natural Gly-Xaa-Yaa-protein of this invention are for example chitosan or oxidized regenerated cellulose (ORC). Optionally the non-natural Gly-Xaa-Yaa-protein of this invention is crosslinked to some extent during or after the sponge formation.

Crosslinking of the non-natural Gly-Xaa-Yaa-protein may be done by any method known in the art. One example is to add a cross-linking agent to the solution of the non-natural Gly-Xaa-Yaa-protein of this invention in water, after which the water is evaporated. The cross-linking agent can also be added after the sponge material is formed by impregnating the sponge with the cross-linking material and evaporating the sponge to dryness. Suitable cross-linking agents are, for example, aldehydes, like glutaraldehyde or a carbodiimide.

The are many medical uses for the sponge according to the invention. The sponge not only can be used for stopping bleeding in very large hemorrhaging areas with a high blood pressure, but also for stopping oozing bleeding. The following internal or external surgical procedures are successfully carried out using the hemostatic sponge according to the invention: general surgery, for instance surgery of parenchymatous organs (liver, kidney, spleen, etc.), cardiovascular surgery, thoracic surgery, transplantation surgery, orthopedic surgery, bone surgery, plastic surgery, ear, nose and throat surgery, neurosurgery, surgery in urology and gynecology as well as haemostasis, such as in wound treatment.

Another embodiment provides a dermal filler comprising the non-natural Gly-Xaa-Yaa-protein as described above. In this application, the non-natural Gly-Xaa-Yaa-proteins are first dissolved in water and than precipitated from the water solution by adding a less hydrophilic solvent like, for example, acetone. During the preparation a cross-linking agent may be present like for example glutaraldehyde, which crosslinks two lysine residues. Another well known biocompatible crosslinker is 1-ethyl-3-(3-dimethylaminopropyl)carbodiimide hydrochloride (EDC).

These cross-linkers or combination of cross-linkers can comprise agents that start cross-linking spontaneously upon addition to polypeptide solution, or after adjusting for example, pH, or by photo-initiation or other activation mechanisms.

Suitable cross-linking agents are preferably those that do not elicit toxic or antigenic effects when released during biodegradation. Suitable cross-linking agents are, for example, one or more of glutaraldehyde, water-soluble carbodiimides, bisepoxy compounds, formalin, 1-ethyl-3-(3-dimethylaminopropyl) carbodiimide, N-hydroxy-succinimide, glycidyl ethers such as alkylene glycol diglycidyl ethers or polyglycerol polyglycidyl ether. Very small particles can be obtained (an average size of from 1 to 500 micron).

These small particles are suitable as injectable tissue fillers or for tissue augmentation or cosmetic surgery. For such applications the average particle size is preferably more than or equal to 100 micron. Average particle sizes in the range of from 150 to 500 are also preferred. Other suitable average particle sizes are 220, 250, 300, 350, 400 and 450 micron. Particles suitable as tissue fillers or augmentors should be deformable so that no lump formation occurs, but a natural impression is obtained after injection of the particles.

The invention also provides a non-natural Gly-Xaa-Yaa-protein as described above for use in the inhibition of cancer metastasis and for the prevention of platelet aggregation or for use after surgery to prevent tissue adhesion.

The non-natural Gly-Xaa-Yaa-proteins according to the invention can be produced by recombinant methods as disclosed in EP-A-0926543, EP-A-1014176 or WO01/34646. Also for enablement of the production and purification of the proteins of the invention reference is made to the examples in EP-A-0926543 and EP-A-1014176 which are herein incorporated by reference.

Thus, the non-natural Gly-Xaa-Yaa-proteins can be produced by expression of a nucleic acid sequence encoding the polypeptide by a suitable micro-organism. Fungal and yeast cells are preferred to bacteria as they are less susceptible to improper expression of repetitive sequences. The process can optimally be carried out with a fungal cell or a yeast cell. Suitably the host cell is a high expression host cell such as *Hansenula*, *Trichoderma*, *Aspergillus*, *Penicillium*, *Saccharomyces*, *Kluyveromyces*, *Neurospora* or *Pichia* sp. Most preferably the host will not have a high level of proteases that attack the expressed protein. The use of methylotrophic yeast cells, such as *Pichia* or *Hansenula* sp. Is preferred. Use of *Pichia pastoris* as an expression system is disclosed in EP-A-0926543 and EP-A-1014176. In one embodiment the microorganism is free of active post-translational processing mechanism such as in particular hydroxylation of proline and also hydroxylation of lysine. In another embodiment the host system has an endogenic proline hydroxylation activity by which the non-natural Gly-Xaa-Yaa-protein is hydroxylated in a highly effective way. The selection of a suitable host cell from known industrial enzyme producing fungal host cells specifically yeast cells on the basis of the required parameters described herein rendering the host cell suitable for expression of non-natural Gly-Xaa-Yaa-protein suitable in compositions according to the invention in combination with knowledge regarding the host cells and the sequence to be expressed will be possible by a person skilled in the art.

Thus, in one aspect the invention a method is provided for producing a non-natural Gly-Xaa-Yaa-protein according to the present invention, said method comprising the steps of
a) preparing an expression vector comprising a nucleic acid sequence encoding a protein as described above operably linked to a suitable promoter,
b) transforming a yeast species with said expression vector,
c) culturing said yeast species under suitable fermentation conditions to allow expression of said nucleic acid sequence;
d) optionally isolating said protein from the culture medium and/or the host cells.

It is preferred that the non-natural Gly-Xaa-Yaa-protein is isolated from the culture medium.

Preferably said non-natural recombinant gelatin is produced at a level of at least 5 g/l supernatant, preferably at least 7 g/l and more preferably in an amount of more than 9 g/l supernatant. Even secretion levels as high as 12, 13, 15 or 17 or 19 g/l or more have been achieved. Preferably the present non-natural Gly-Xaa-Yaa-protein is isolated and purified.

Also mutant host strains may be used, e.g. strains deficient in one or more proteolytic enzymes, although this is not necessary according to the present invention, as the recombinant polypeptides are highly stable and resistant to proteolysis.

The invention will be explained in more detail in the following, non-limiting examples:

SEQUENCES

SEQ ID 1: Sequence of ICP monomer.
SEQ ID 2: Sequence of ICP-dimer.
SEQ ID 3: Sequence of ICP-tetramer.
SEQ ID 4: Sequence of ICP.
SEQ ID 5: Sequence of ICP2.
SEQ ID 6: Sequence of ICP3.
SEQ ID 7: Sequence of ICP4.
SEQ ID 8: Sequence of plasmid pFFZα A.
SEQ ID 9: Sequence of ICP3 variant 1.
SEQ ID 10: Sequence of ICP3 variant 2
SEQ ID 11: Sequence of ICP3 variant 3
SEQ ID 12: Sequence of ICP3 variant 4
SEQ ID 13: Sequence of ICP3 variant 6

SEQ ID 14: Sequence of ICP3 variant 7
SEQ ID 15: Sequence of ICP3 variant 8

EXAMPLES

FIG. 1 shows SDS PAGE analysis of representative culture supernatants of the host cells (CBS 7435) and of strains that produce ICP3 and its variants ICP3-var6 and ICP3-var8. Arrows indicate the mature protein.

Strains and Genetic Vectors Used

In the examples, *Pichia pastoris* strain CBS7435 was used as the host strain. Plasmid pFFZαA was used as the vector for the genes that encode synthetic gelatins. It contains the following elements: an origin of replication for plasmid maintenance in *E. coli*, a zeocin resistance marker that can be used in either *E. coli* or *Pichia pastoris* and the AOX1 promoter, the AOX1 terminator and the prepro sequence of the yeast pheromone mating factor alpha from *Saccharomyces cerevisiae* to control methanol-induced expression and secretion of a gene of interest. The DNA sequence of the plasmid is disclosed as SEQ ID 8.

Preparation of the Genetic Construct for Production of a Gelatine-Like Protein

A synthetic gelatin named ICP3 was designed for enhanced cell-binding. The sequence of ICP3 is disclosed as SEQ ID 6. The sequence is enriched in the cell-binding sequence RGD.

The codon-optimized gene for the synthetic gelatin ICP3 was synthesized. This gene was subcloned as a XhoI-XbaI fragment in pFFZαA digested with the same enzymes. This resulted in plasmid pFFZ-ICP3. This plasmids contain a gene that encodes MFα-ICP3, in which the ICP3 gelatin sequence is fused to the prepro sequence of mating factor alpha. Host cells that contain this plasmid were used to produce and secrete MFα-ICP3. The principles of the production and secretion of heterologous proteins in *Pichia pastoris* and their maturation (removal of the secretion signal) are well known in the art.

Transformation of the Host Cells

Plasmid pFFZ-ICP3 was linearized with restriction enzyme PmeI to promote integration in the AOX1 promoter of the host cell. The linearized plasmid was introduced in the host cell by electroporation. Transformants were selected by plating the transformation mixture on YPD agar plates (10 g/l yeast extract, 20 g/l peptone, 20 g/l dextrose and 20 g/l agar in water) supplemented with zeocin at a concentration of 0.5 mg/ml Recombinant Production of the Gelatine-Like Protein ICP3 production by several transformants was analyzed in shake flask cultures as follows. Erlenmeyers (100 mL) were filled with 10 mL of YPD medium (10 g/l yeast extract, 20 g/l peptone and 20 g/l dextrose in water). These cultures were inoculated with cells from the colonies that appeared after the transformation. The culture was allowed to reach saturation overnight. The next day, the cells were harvested by centrifugation (3000×g, 10 minutes) and the spent medium was decanted. The cells were resuspended in buffered minimal methanol medium (100 mM potassium phosphate, pH 6.0, 1.34% Yeast Nitrogen Base, $4 \times 10^{-5}$% biotin, 0.5% methanol) and grown on this medium overnight. The next two days, methanol was added to each culture to a final concentration of 1%. On the fifth day, the cells were removed by centrifugation and the supernatant was analyzed by sodium dodecyl sulfate polyacrylamide gel electrophoresis (SDS-PAGE), using the Multiphor II electrophoresis system (GE Healthcare). ICP3 production by a few representative transformants is shown in FIG. 1A. For comparison, supernatants of two cultures of the host strain grown under the same conditions are also shown.

From FIG. 1, it can be inferred that the ICP3 product is accompanied by several smaller proteolytic degradation products.

Characterization of the Degradation Products

In order to identify the cleavage sites, it was decided to perform mass spectrometry. Since ICP3 has a very repetitive sequence, mass spectrometry was performed on ICP, rather than on ICP3. The sequence of ICP is disclosed as SEQ ID 4. ICP was produced with the methods described above and was partly purified by anion exchange chromatography. Analytical liquid chromatography coupled mass spectrometry (LC-MS) was used to determine the masses of the intact protein ICP3 and its degradation products. The theoretical mass of ICP is 17617 Dalton.

The molecular masses that were obtained are listed in Table 1.

| RT (min) | MW (Da) |
|---|---|
| 15.6 | 11891 |
| 15.6 | 9387 |
| 15.6 | 11450 |
| 15.6 | 17664 |
| 15.6 | 9458 |
| 15.6 | 8175 |
| 15.6 | 14442 |
| 16.9 | 12412 |
| 16.9 | 12212 |
| 16.9 | 14442 |
| 17.5 | 17648 |
| 17.5 | 10198 |
| 17.5 | 17600 |
| 17.5 | 9048 |
| 17.5 | 9306 |
| 18.5 | 17648 |
| 18.5 | 14427 |
| 18.5 | 12061 |
| 18.5 | 17600 |
| 19.8 | 17632 |
| 19.8 | 17584 |
| 20.8 | 17631 |
| 20.8 | 17583 |
| 20.8 | 17092 |
| 20.8 | 17035 |
| 20.8 | 18430 |
| 21.4 | 17616 |
| 24.8 | 17206 |
| 24.8 | 17617 |
| 24.8 | 15344 |
| 24.8 | 15342 |

The observed masses were compared with the masses that could theoretically be obtained from ICP. This analysis suggested that the sequences GLAG and GAAG are particularly susceptible to proteolytic cleavage. In addition, proteolysis frequently occurs after the sequence GER, depending on amino acids C-terminal of the arginine residue. Proteolysis was also found to occur behind the lysine residue in the sequence PGKEGV. In addition, the LC-MS data suggest that cleavage occurs after certain aspartic acid residues.

Development of Variants that are Resistant to Proteolysis

To develop recombinant gelatine-like proteins more resistant to this proteolytic degradation and to determine which sequences are targeted by proteolytic activity a series of variants of ICP3 (SEQ IDs 9-15) was designed and synthesized. These variants were produced and analyzed by SDS-PAGE as described above.

Variants 1, 2, 3 and 4 (SEQ IDs 9-12) contain mutations around the RGD and GER sequences. However, these variants showed no significant reduction in the number of degradation bands, as compared to the original ICP3.

ICP3 variant 6 (SEQ ID 13) is identical to ICP3, except that all GLA triplets have been deleted. ICP3 variant 8 (SEQ ID 15) is identical to ICP3 variant 6, except that all GAA triplets have been replaced with GAP triplets. Surprisingly the removal of the GLA triplets and substitution of the GAA triplets by GAP triplets virtually abolishes the degradation bands that were observed for the original ICP3 protein, as can be seen from FIG. 1B. ICP3 variant 7 (SEQ ID 14) is identical to ICP3 with exception of the RGD triplets, which have been deleted to limit the number of aspartic acid residues. However, this variant showed an unwanted increase in degradation, most certainly caused by the increased overall hydrophobicity of this variant.

The invention claimed is:

1. A non-natural Gly-Xaa-Yaa-protein having a molecular weight of at least 5 kDa, wherein at least 80% of the amino acids are present as Gly-Xaa-Yaa triplets, wherein Gly is glycine and Xaa and Yaa are, independently, any amino acid, wherein said protein lacks the sequences GLA and GAA and has a calculated iso-electric point of at least 7, and wherein the nimber percent of aspartic acid residues, apart from those residues which are present in the RGD motifs, is below 1.

2. The non-natural Gly-Xaa-Yaa-protein according to claim 1 free of serine and threonine amino acid residues.

3. The non-natural Gly-Xaa-Yaa-protein according to claim 1 comprising at least one XRGD motif per 5 kDa molecular weight of sequence, wherein X is any amino acid with the exception of D (Asp) and P (Pro) or O (hydroxyproline).

4. The non-natural Gly-Xaa-Yaa-protein according to claim 3, wherein X is selected from the group consisting of Y, W, F, C, M, K, L, I, R, H, V, A, G, N and E.

5. The non-natural Gly-Xaa-Yaa-protein according to claim 3, wheren each 5 kDa part of the non-natural Gly-Xaa-Yaa-protein comprises at least two XRGD motifs.

6. The non-natural Gly-Xaa-Yaa-protein according to claim 1 wherein less than 5%, of the amino acid residues are hydroxyprolines.

7. The non-natural Gly-Xaa-Yaa-protein according to claim 1, which has at least 85% sequence identity to SEQ ID NO: 1.

8. A non-natural Gly-Xaa-Yaa-protein comprising or consisting of at least two repeats of a non-natural Gly-Xaa-Yaa-protein according to claim 1.

9. The polymeric non-natural Gly-Xaa-Yaa-protein according to claim 8, wherein said repeats are repeats of the same monomer unit sequence.

10. The polymeric non-natural Gly-Xaa-Yaa-protein according to claim 8, wherein there are less than 7 intervening amino acids between the monomer repeat units.

11. A cell support comprising a non-natural Gly-Xaa-Yaa-protein as described in claim 1.

12. The cell support according to claim 11, said cell support being selected from the group consisting of a non-natural Gly-Xaa-Yaa-protein coated implant or transplant material, a non-natural Gly-Xaa-Yaa-protein coated scaffold for tissue engineering, (part of) a dental product, (part of) a wound healing product, (part of) artificial skin matrix material and (part of) a tissue adhesive.

13. A controlled release composition comprising a non-natural Gly-Xaa-Yaa-protein as described in claim 1.

14. A hemostat composition comprising a non-natural Gly-Xaa-Yaa-protein as described in claim 1.

15. A dermal filler composition comprising a non-natural Gly-Xaa-Yaa-protein as described in claim 1.

16. The non-natural Gly-Xaa-Yaa-protein as described in claim 1 for use in the inhibition of cancer metastasis and for the prevention of platelet aggregation or after surgery to prevent tissue adhesion.

17. The controlled release composition as described in claim 13 for use in the treatment of pain, cancer therapy, cardiovascular diseases, myocardial repair, angiogenesis, bone repair and regeneration, wound treatment, neural stimulation/therapy and diabetics.

18. A method for producing a non-natural Gly-Xaa-Yaa-protein as described in claim 1, said method comprising the steps of:
   a) preparing an expression vector comprising a nucleic acid sequence encoding a protein according to claim 1 operably linked to a suitable promoter,
   b) transforming a yeast species with said expression vector,
   c) culturing said yeast species under suitable fermentation conditions to allow expression of said nucleic acid sequence;
   d) optionally isolating said protein from the culture medium and/or the host cells.

* * * * *

SEQUENCE LISTING

```
<160> NUMBER OF SEQ ID NOS: 15

<210> SEQ ID NO 1
<211> LENGTH: 189
<212> TYPE: PRT
<213> ORGANISM: Artificial
<220> FEATURE:
<223> OTHER INFORMATION: Sequence of ICP monomer

<400> SEQUENCE: 1

Gly Ala Pro Gly Leu Gln Gly Ala Pro Gly Leu Gln Gly Met Pro Gly
1               5                   10                  15

Glu Arg Gly Ala Ala Gly Leu Pro Gly Pro Lys Gly Glu Arg Gly Asp
                20                  25                  30

Val Gly Pro Lys Gly Ala Glu Gly Ala Pro Gly Ala Pro Gly Leu Gln
            35                  40                  45

Gly Met Pro Gly Glu Arg Gly Ala Ala Gly Leu Pro Gly Pro Lys Gly
        50                  55                  60

Glu Arg Gly Asp Lys Gly Pro Lys Gly Ala Glu Gly Ala Pro Gly Lys
65                  70                  75                  80

Glu Gly Val Arg Gly Leu Ala Gly Pro Ile Gly Pro Pro Gly Glu Arg
                85                  90                  95

Gly Ala Ala Gly Leu Pro Gly Pro Lys Gly Glu Arg Gly Asp Glu Gly
                100                 105                 110

Pro Lys Gly Ala Glu Gly Ala Pro Gly Lys Glu Gly Val Arg Gly Leu
            115                 120                 125

Ala Gly Pro Ile Gly Pro Pro Gly Pro Ala Gly Ala Pro Gly Ala Pro
        130                 135                 140

Gly Leu Gln Gly Met Pro Gly Glu Arg Gly Ala Ala Gly Leu Pro Gly
145                 150                 155                 160

Pro Lys Gly Glu Arg Gly Asp Gln Gly Pro Lys Gly Ala Glu Gly Ala
                165                 170                 175

Pro Gly Lys Glu Gly Val Arg Gly Leu Ala Gly Pro Ala
            180                 185

<210> SEQ ID NO 2
<211> LENGTH: 378
<212> TYPE: PRT
<213> ORGANISM: Artificial
<220> FEATURE:
<223> OTHER INFORMATION: Sequence of ICP-dimer

<400> SEQUENCE: 2

Gly Ala Pro Gly Leu Gln Gly Ala Pro Gly Leu Gln Gly Met Pro Gly
1               5                   10                  15

Glu Arg Gly Ala Ala Gly Leu Pro Gly Pro Lys Gly Glu Arg Gly Asp
                20                  25                  30

Val Gly Pro Lys Gly Ala Glu Gly Ala Pro Gly Ala Pro Gly Leu Gln
            35                  40                  45

Gly Met Pro Gly Glu Arg Gly Ala Ala Gly Leu Pro Gly Pro Lys Gly
        50                  55                  60
```

Glu Arg Gly Asp Lys Gly Pro Lys Gly Ala Glu Ala Pro Gly Lys
65                  70                  75                  80

Glu Gly Val Arg Gly Leu Ala Gly Pro Ile Gly Pro Pro Gly Glu Arg
            85                  90                  95

Gly Ala Ala Gly Leu Pro Gly Pro Lys Gly Glu Arg Gly Asp Glu Gly
            100                 105                 110

Pro Lys Gly Ala Glu Gly Ala Pro Gly Lys Glu Gly Val Arg Gly Leu
        115                 120                 125

Ala Gly Pro Ile Gly Pro Pro Gly Pro Ala Gly Ala Pro Gly Ala Pro
        130                 135                 140

Gly Leu Gln Gly Met Pro Gly Glu Arg Gly Ala Ala Gly Leu Pro Gly
145                 150                 155                 160

Pro Lys Gly Glu Arg Gly Asp Gln Gly Pro Lys Gly Ala Glu Gly Ala
            165                 170                 175

Pro Gly Lys Glu Gly Val Arg Gly Leu Ala Gly Pro Ala Gly Ala Pro
            180                 185                 190

Gly Leu Gln Gly Ala Pro Gly Leu Gln Gly Met Pro Gly Glu Arg Gly
        195                 200                 205

Ala Ala Gly Leu Pro Gly Pro Lys Gly Glu Arg Gly Asp Val Gly Pro
210                 215                 220

Lys Gly Ala Glu Gly Ala Pro Gly Ala Pro Gly Leu Gln Gly Met Pro
225                 230                 235                 240

Gly Glu Arg Gly Ala Ala Gly Leu Pro Gly Pro Lys Gly Glu Arg Gly
            245                 250                 255

Asp Lys Gly Pro Lys Gly Ala Glu Gly Ala Pro Gly Lys Glu Gly Val
            260                 265                 270

Arg Gly Leu Ala Gly Pro Ile Gly Pro Pro Gly Glu Arg Gly Ala Ala
        275                 280                 285

Gly Leu Pro Gly Pro Lys Gly Glu Arg Gly Asp Glu Gly Pro Lys Gly
        290                 295                 300

Ala Glu Gly Ala Pro Gly Lys Glu Gly Val Arg Gly Leu Ala Gly Pro
305                 310                 315                 320

Ile Gly Pro Pro Gly Pro Ala Gly Ala Pro Gly Ala Pro Gly Leu Gln
            325                 330                 335

Gly Met Pro Gly Glu Arg Gly Ala Ala Gly Leu Pro Gly Pro Lys Gly
            340                 345                 350

Glu Arg Gly Asp Gln Gly Pro Lys Gly Ala Glu Gly Ala Pro Gly Lys
        355                 360                 365

Glu Gly Val Arg Gly Leu Ala Gly Pro Ala
        370                 375

<210> SEQ ID NO 3
<211> LENGTH: 756
<212> TYPE: PRT
<213> ORGANISM: Artificial
<220> FEATURE:
<223> OTHER INFORMATION: Sequence of ICP-tetramer

<400> SEQUENCE: 3

Gly Ala Pro Gly Leu Gln Gly Ala Pro Gly Leu Gln Gly Met Pro Gly
1               5                   10                  15

Glu Arg Gly Ala Ala Gly Leu Pro Gly Pro Lys Gly Glu Arg Gly Asp
            20                  25                  30

Val Gly Pro Lys Gly Ala Glu Gly Ala Pro Gly Ala Pro Gly Leu Gln
        35                  40                  45

```
Gly Met Pro Gly Glu Arg Gly Ala Ala Gly Leu Pro Gly Pro Lys Gly
     50                  55                  60

Glu Arg Gly Asp Lys Gly Pro Lys Gly Glu Gly Ala Pro Gly Lys
 65                  70                  75                  80

Glu Gly Val Arg Gly Leu Ala Gly Pro Ile Gly Pro Pro Gly Glu Arg
             85                  90                  95

Gly Ala Ala Gly Leu Pro Gly Pro Lys Gly Glu Arg Gly Asp Glu Gly
            100                 105                 110

Pro Lys Gly Ala Glu Gly Ala Pro Gly Lys Glu Gly Val Arg Gly Leu
            115                 120                 125

Ala Gly Pro Ile Gly Pro Pro Gly Pro Ala Gly Ala Pro Gly Ala Pro
130                 135                 140

Gly Leu Gln Gly Met Pro Gly Glu Arg Gly Ala Ala Gly Leu Pro Gly
145                 150                 155                 160

Pro Lys Gly Glu Arg Gly Asp Gln Gly Pro Lys Gly Ala Glu Gly Ala
                165                 170                 175

Pro Gly Lys Glu Gly Val Arg Gly Leu Ala Gly Pro Ala Gly Ala Pro
            180                 185                 190

Gly Leu Gln Gly Ala Pro Gly Leu Gln Gly Met Pro Gly Glu Arg Gly
            195                 200                 205

Ala Ala Gly Leu Pro Gly Pro Lys Gly Glu Arg Gly Asp Val Gly Pro
210                 215                 220

Lys Gly Ala Glu Gly Ala Pro Gly Ala Pro Gly Leu Gln Gly Met Pro
225                 230                 235                 240

Gly Glu Arg Gly Ala Ala Gly Leu Pro Gly Pro Lys Gly Glu Arg Gly
                245                 250                 255

Asp Lys Gly Pro Lys Gly Ala Glu Gly Ala Pro Gly Lys Glu Gly Val
            260                 265                 270

Arg Gly Leu Ala Gly Pro Ile Gly Pro Pro Gly Glu Arg Gly Ala Ala
            275                 280                 285

Gly Leu Pro Gly Pro Lys Gly Glu Arg Gly Asp Glu Gly Pro Lys Gly
290                 295                 300

Ala Glu Gly Ala Pro Gly Lys Glu Gly Val Arg Gly Leu Ala Gly Pro
305                 310                 315                 320

Ile Gly Pro Pro Gly Pro Ala Gly Ala Pro Gly Ala Pro Gly Leu Gln
                325                 330                 335

Gly Met Pro Gly Glu Arg Gly Ala Ala Gly Leu Pro Gly Pro Lys Gly
            340                 345                 350

Glu Arg Gly Asp Gln Gly Pro Lys Gly Ala Glu Gly Ala Pro Gly Lys
            355                 360                 365

Glu Gly Val Arg Gly Leu Ala Gly Pro Ala Gly Ala Pro Gly Leu Gln
            370                 375                 380

Gly Ala Pro Gly Leu Gln Gly Met Pro Gly Glu Arg Gly Ala Ala Gly
385                 390                 395                 400

Leu Pro Gly Pro Lys Gly Glu Arg Gly Asp Val Gly Pro Lys Gly Ala
                405                 410                 415

Glu Gly Ala Pro Gly Ala Pro Gly Leu Gln Gly Met Pro Gly Glu Arg
            420                 425                 430

Gly Ala Ala Gly Leu Pro Gly Pro Lys Gly Glu Arg Gly Asp Lys Gly
            435                 440                 445

Pro Lys Gly Ala Glu Gly Ala Pro Gly Lys Glu Gly Val Arg Gly Leu
450                 455                 460

Ala Gly Pro Ile Gly Pro Pro Gly Glu Arg Gly Ala Ala Gly Leu Pro
```

```
                465                 470                 475                 480
Gly Pro Lys Gly Glu Arg Gly Asp Glu Gly Pro Lys Gly Ala Glu Gly
                    485                 490                 495

Ala Pro Gly Lys Glu Gly Val Arg Gly Leu Ala Gly Pro Ile Gly Pro
                500                 505                 510

Pro Gly Pro Ala Gly Ala Pro Gly Ala Pro Gly Leu Gln Gly Met Pro
            515                 520                 525

Gly Glu Arg Gly Ala Ala Gly Leu Pro Gly Pro Lys Gly Glu Arg Gly
        530                 535                 540

Asp Gln Gly Pro Lys Gly Ala Glu Gly Ala Pro Gly Lys Glu Gly Val
545                 550                 555                 560

Arg Gly Leu Ala Gly Pro Ala Gly Ala Pro Gly Leu Gln Gly Ala Pro
                565                 570                 575

Gly Leu Gln Gly Met Pro Gly Glu Arg Gly Ala Ala Gly Leu Pro Gly
                580                 585                 590

Pro Lys Gly Glu Arg Gly Asp Val Gly Pro Lys Gly Ala Glu Gly Ala
            595                 600                 605

Pro Gly Ala Pro Gly Leu Gln Gly Met Pro Gly Glu Arg Gly Ala Ala
        610                 615                 620

Gly Leu Pro Gly Pro Lys Gly Glu Arg Gly Asp Lys Gly Pro Lys Gly
625                 630                 635                 640

Ala Glu Gly Ala Pro Gly Lys Glu Gly Val Arg Gly Leu Ala Gly Pro
                645                 650                 655

Ile Gly Pro Pro Gly Glu Arg Gly Ala Ala Gly Leu Pro Gly Pro Lys
                660                 665                 670

Gly Glu Arg Gly Asp Glu Gly Pro Lys Gly Ala Glu Gly Ala Pro Gly
            675                 680                 685

Lys Glu Gly Val Arg Gly Leu Ala Gly Pro Ile Gly Pro Pro Gly Pro
        690                 695                 700

Ala Gly Ala Pro Gly Ala Pro Gly Leu Gln Gly Met Pro Gly Glu Arg
705                 710                 715                 720

Gly Ala Ala Gly Leu Pro Gly Pro Lys Gly Glu Arg Gly Asp Gln Gly
                725                 730                 735

Pro Lys Gly Ala Glu Gly Ala Pro Gly Lys Glu Gly Val Arg Gly Leu
            740                 745                 750

Ala Gly Pro Ala
        755

<210> SEQ ID NO 4
<211> LENGTH: 194
<212> TYPE: PRT
<213> ORGANISM: Artificial
<220> FEATURE:
<223> OTHER INFORMATION: Sequence of ICP

<400> SEQUENCE: 4

Gly Pro Pro Gly Ala Pro Gly Leu Gln Gly Ala Pro Gly Leu Gln Gly
1               5                   10                  15

Met Pro Gly Glu Arg Gly Ala Ala Gly Leu Pro Gly Pro Lys Gly Glu
            20                  25                  30

Arg Gly Asp Val Gly Pro Lys Gly Ala Glu Gly Ala Pro Gly Ala Pro
        35                  40                  45

Gly Leu Gln Gly Met Pro Gly Glu Arg Gly Ala Ala Gly Leu Pro Gly
    50                  55                  60

Pro Lys Gly Glu Arg Gly Asp Lys Gly Pro Lys Gly Ala Glu Gly Ala
```

```
                65                  70                  75                  80
Pro Gly Lys Glu Gly Val Arg Gly Leu Ala Gly Pro Ile Gly Pro Pro
                    85                  90                  95

Gly Glu Arg Gly Ala Ala Gly Leu Pro Gly Pro Lys Gly Glu Arg Gly
                100                 105                 110

Asp Glu Gly Pro Lys Gly Ala Glu Gly Ala Pro Gly Lys Glu Gly Val
                115                 120                 125

Arg Gly Leu Ala Gly Pro Ile Gly Pro Pro Gly Pro Ala Gly Ala Pro
            130                 135                 140

Gly Ala Pro Gly Leu Gln Gly Met Pro Gly Glu Arg Gly Ala Ala Gly
145                 150                 155                 160

Leu Pro Gly Pro Lys Gly Glu Arg Gly Asp Gln Gly Pro Lys Gly Ala
                165                 170                 175

Glu Gly Ala Pro Gly Lys Glu Gly Val Arg Gly Leu Ala Gly Pro Ala
                180                 185                 190

Gly Gly

<210> SEQ ID NO 5
<211> LENGTH: 383
<212> TYPE: PRT
<213> ORGANISM: Artificial
<220> FEATURE:
<223> OTHER INFORMATION: Sequence of ICP2

<400> SEQUENCE: 5

Gly Pro Pro Gly Ala Pro Gly Leu Gln Gly Ala Pro Gly Leu Gln Gly
1               5                   10                  15

Met Pro Gly Glu Arg Gly Ala Ala Gly Leu Pro Gly Pro Lys Gly Glu
                20                  25                  30

Arg Gly Asp Val Gly Pro Lys Gly Ala Glu Gly Ala Pro Gly Ala Pro
            35                  40                  45

Gly Leu Gln Gly Met Pro Gly Glu Arg Gly Ala Ala Gly Leu Pro Gly
        50                  55                  60

Pro Lys Gly Glu Arg Gly Asp Lys Gly Pro Lys Gly Ala Glu Gly Ala
65                  70                  75                  80

Pro Gly Lys Glu Gly Val Arg Gly Leu Ala Gly Pro Ile Gly Pro Pro
                85                  90                  95

Gly Glu Arg Gly Ala Ala Gly Leu Pro Gly Pro Lys Gly Glu Arg Gly
                100                 105                 110

Asp Glu Gly Pro Lys Gly Ala Glu Gly Ala Pro Gly Lys Glu Gly Val
                115                 120                 125

Arg Gly Leu Ala Gly Pro Ile Gly Pro Pro Gly Pro Ala Gly Ala Pro
            130                 135                 140

Gly Ala Pro Gly Leu Gln Gly Met Pro Gly Glu Arg Gly Ala Ala Gly
145                 150                 155                 160

Leu Pro Gly Pro Lys Gly Glu Arg Gly Asp Gln Gly Pro Lys Gly Ala
                165                 170                 175

Glu Gly Ala Pro Gly Lys Glu Gly Val Arg Gly Leu Ala Gly Pro Ala
                180                 185                 190

Gly Ala Pro Gly Leu Gln Gly Ala Pro Gly Leu Gln Gly Met Pro Gly
            195                 200                 205

Glu Arg Gly Ala Ala Gly Leu Pro Gly Pro Lys Gly Glu Arg Gly Asp
        210                 215                 220

Val Gly Pro Lys Gly Ala Glu Gly Ala Pro Gly Ala Pro Gly Leu Gln
225                 230                 235                 240
```

```
Gly Met Pro Gly Glu Arg Gly Ala Ala Gly Leu Pro Gly Pro Lys Gly
            245                 250                 255

Glu Arg Gly Asp Lys Gly Pro Lys Gly Ala Glu Gly Ala Pro Gly Lys
        260                 265                 270

Glu Gly Val Arg Gly Leu Ala Gly Pro Ile Gly Pro Pro Gly Glu Arg
        275                 280                 285

Gly Ala Ala Gly Leu Pro Gly Pro Lys Gly Glu Arg Gly Asp Glu Gly
        290                 295                 300

Pro Lys Gly Ala Glu Gly Ala Pro Gly Lys Glu Gly Val Arg Gly Leu
305                 310                 315                 320

Ala Gly Pro Ile Gly Pro Pro Gly Pro Ala Gly Ala Pro Gly Ala Pro
                325                 330                 335

Gly Leu Gln Gly Met Pro Gly Glu Arg Gly Ala Ala Gly Leu Pro Gly
                340                 345                 350

Pro Lys Gly Glu Arg Gly Asp Gln Gly Pro Lys Gly Ala Glu Gly Ala
            355                 360                 365

Pro Gly Lys Glu Gly Val Arg Gly Leu Ala Gly Pro Ala Gly Gly
            370                 375                 380

<210> SEQ ID NO 6
<211> LENGTH: 572
<212> TYPE: PRT
<213> ORGANISM: Artificial
<220> FEATURE:
<223> OTHER INFORMATION: Sequence of ICP3

<400> SEQUENCE: 6

Gly Pro Pro Gly Ala Pro Gly Leu Gln Gly Ala Pro Gly Leu Gln Gly
1               5                   10                  15

Met Pro Gly Glu Arg Gly Ala Ala Gly Leu Pro Gly Pro Lys Gly Glu
            20                  25                  30

Arg Gly Asp Val Gly Pro Lys Gly Ala Glu Gly Ala Pro Gly Ala Pro
        35                  40                  45

Gly Leu Gln Gly Met Pro Gly Glu Arg Gly Ala Ala Gly Leu Pro Gly
    50                  55                  60

Pro Lys Gly Glu Arg Gly Asp Lys Gly Pro Lys Gly Ala Glu Gly Ala
65                  70                  75                  80

Pro Gly Lys Glu Gly Val Arg Gly Leu Ala Gly Pro Ile Gly Pro Pro
                85                  90                  95

Gly Glu Arg Gly Ala Ala Gly Leu Pro Gly Pro Lys Gly Glu Arg Gly
            100                 105                 110

Asp Glu Gly Pro Lys Gly Ala Glu Gly Ala Pro Gly Lys Glu Gly Val
        115                 120                 125

Arg Gly Leu Ala Gly Pro Ile Gly Pro Pro Gly Pro Ala Gly Ala Pro
    130                 135                 140

Gly Ala Pro Gly Leu Gln Gly Met Pro Gly Glu Arg Gly Ala Ala Gly
145                 150                 155                 160

Leu Pro Gly Pro Lys Gly Glu Arg Gly Asp Gln Gly Pro Lys Gly Ala
                165                 170                 175

Glu Gly Ala Pro Gly Lys Glu Gly Val Arg Gly Leu Ala Gly Pro Ala
            180                 185                 190

Gly Ala Pro Gly Leu Gln Gly Ala Pro Gly Leu Gln Gly Met Pro Gly
        195                 200                 205

Glu Arg Gly Ala Ala Gly Leu Pro Gly Pro Lys Gly Glu Arg Gly Asp
    210                 215                 220
```

```
Val Gly Pro Lys Gly Ala Glu Gly Ala Pro Gly Ala Pro Gly Leu Gln
225                 230                 235                 240

Gly Met Pro Gly Glu Arg Gly Ala Ala Gly Leu Pro Gly Pro Lys Gly
            245                 250                 255

Glu Arg Gly Asp Lys Gly Pro Lys Gly Ala Glu Gly Ala Pro Gly Lys
        260                 265                 270

Glu Gly Val Arg Gly Leu Ala Gly Pro Ile Gly Pro Pro Gly Glu Arg
    275                 280                 285

Gly Ala Ala Gly Leu Pro Gly Pro Lys Gly Glu Arg Gly Asp Glu Gly
290                 295                 300

Pro Lys Gly Ala Glu Gly Ala Pro Gly Lys Gly Val Arg Gly Leu
305                 310                 315                 320

Ala Gly Pro Ile Gly Pro Pro Gly Pro Ala Gly Ala Pro Gly Ala Pro
                325                 330                 335

Gly Leu Gln Gly Met Pro Gly Glu Arg Gly Ala Ala Gly Leu Pro Gly
            340                 345                 350

Pro Lys Gly Glu Arg Gly Asp Gln Gly Pro Lys Gly Ala Glu Gly Ala
        355                 360                 365

Pro Gly Lys Glu Gly Val Arg Gly Leu Ala Gly Pro Ala Gly Ala Pro
    370                 375                 380

Gly Leu Gln Gly Ala Pro Gly Leu Gln Gly Met Pro Gly Glu Arg Gly
385                 390                 395                 400

Ala Ala Gly Leu Pro Gly Pro Lys Gly Glu Arg Gly Asp Val Gly Pro
                405                 410                 415

Lys Gly Ala Glu Gly Ala Pro Gly Ala Pro Gly Leu Gln Gly Met Pro
            420                 425                 430

Gly Glu Arg Gly Ala Ala Gly Leu Pro Gly Pro Lys Gly Glu Arg Gly
        435                 440                 445

Asp Lys Gly Pro Lys Gly Ala Glu Gly Ala Pro Gly Lys Glu Gly Val
    450                 455                 460

Arg Gly Leu Ala Gly Pro Ile Gly Pro Pro Gly Glu Arg Gly Ala Ala
465                 470                 475                 480

Gly Leu Pro Gly Pro Lys Gly Glu Arg Gly Asp Glu Gly Pro Lys Gly
                485                 490                 495

Ala Glu Gly Ala Pro Gly Lys Glu Gly Val Arg Gly Leu Ala Gly Pro
            500                 505                 510

Ile Gly Pro Pro Gly Pro Ala Gly Ala Pro Gly Ala Pro Gly Leu Gln
        515                 520                 525

Gly Met Pro Gly Glu Arg Gly Ala Ala Gly Leu Pro Gly Pro Lys Gly
    530                 535                 540

Glu Arg Gly Asp Gln Gly Pro Lys Gly Ala Glu Gly Ala Pro Gly Lys
545                 550                 555                 560

Glu Gly Val Arg Gly Leu Ala Gly Pro Ala Gly Gly
                565                 570

<210> SEQ ID NO 7
<211> LENGTH: 761
<212> TYPE: PRT
<213> ORGANISM: Artificial
<220> FEATURE:
<223> OTHER INFORMATION: Sequence of ICP4

<400> SEQUENCE: 7

Gly Pro Pro Gly Ala Pro Gly Leu Gln Gly Ala Pro Gly Leu Gln Gly
1               5                   10                  15
```

```
Met Pro Gly Glu Arg Gly Ala Ala Gly Leu Pro Gly Pro Lys Gly Glu
             20                  25                  30
Arg Gly Asp Val Gly Pro Lys Gly Ala Glu Gly Ala Pro Gly Ala Pro
         35                  40                  45
Gly Leu Gln Gly Met Pro Gly Glu Arg Gly Ala Ala Gly Leu Pro Gly
 50                  55                  60
Pro Lys Gly Glu Arg Gly Asp Lys Gly Pro Lys Gly Ala Glu Gly Ala
65                  70                  75                  80
Pro Gly Lys Glu Gly Val Arg Gly Leu Ala Gly Pro Ile Gly Pro Pro
                 85                  90                  95
Gly Glu Arg Gly Ala Ala Gly Leu Pro Gly Pro Lys Gly Glu Arg Gly
            100                 105                 110
Asp Glu Gly Pro Lys Gly Ala Glu Gly Ala Pro Gly Lys Glu Gly Val
        115                 120                 125
Arg Gly Leu Ala Gly Pro Ile Gly Pro Pro Gly Pro Ala Gly Ala Pro
130                 135                 140
Gly Ala Pro Gly Leu Gln Gly Met Pro Gly Glu Arg Gly Ala Ala Gly
145                 150                 155                 160
Leu Pro Gly Pro Lys Gly Glu Arg Gly Asp Gln Gly Pro Lys Gly Ala
                165                 170                 175
Glu Gly Ala Pro Gly Lys Glu Gly Val Arg Gly Leu Ala Gly Pro Ala
            180                 185                 190
Gly Ala Pro Gly Leu Gln Gly Ala Pro Gly Leu Gln Gly Met Pro Gly
        195                 200                 205
Glu Arg Gly Ala Ala Gly Leu Pro Gly Pro Lys Gly Glu Arg Gly Asp
210                 215                 220
Val Gly Pro Lys Gly Ala Glu Gly Ala Pro Gly Ala Pro Gly Leu Gln
225                 230                 235                 240
Gly Met Pro Gly Glu Arg Gly Ala Ala Gly Leu Pro Gly Pro Lys Gly
                245                 250                 255
Glu Arg Gly Asp Lys Gly Pro Lys Gly Ala Glu Gly Ala Pro Gly Lys
            260                 265                 270
Glu Gly Val Arg Gly Leu Ala Gly Pro Ile Gly Pro Pro Gly Glu Arg
        275                 280                 285
Gly Ala Ala Gly Leu Pro Gly Pro Lys Gly Glu Arg Gly Asp Glu Gly
290                 295                 300
Pro Lys Gly Ala Glu Gly Ala Pro Gly Lys Glu Gly Val Arg Gly Leu
305                 310                 315                 320
Ala Gly Pro Ile Gly Pro Pro Gly Pro Ala Gly Ala Pro Gly Ala Pro
                325                 330                 335
Gly Leu Gln Gly Met Pro Gly Glu Arg Gly Ala Ala Gly Leu Pro Gly
            340                 345                 350
Pro Lys Gly Glu Arg Gly Asp Gln Gly Pro Lys Gly Ala Glu Gly Ala
        355                 360                 365
Pro Gly Lys Glu Gly Val Arg Gly Leu Ala Gly Pro Ala Gly Ala Pro
370                 375                 380
Gly Leu Gln Gly Ala Pro Gly Leu Gln Gly Met Pro Gly Glu Arg Gly
385                 390                 395                 400
Ala Ala Gly Leu Pro Gly Pro Lys Gly Glu Arg Gly Asp Val Gly Pro
                405                 410                 415
Lys Gly Ala Glu Gly Ala Pro Gly Ala Pro Gly Leu Gln Gly Met Pro
            420                 425                 430
```

```
Gly Glu Arg Gly Ala Ala Gly Leu Pro Gly Pro Lys Gly Glu Arg Gly
                435                 440                 445

Asp Lys Gly Pro Lys Gly Ala Glu Gly Ala Pro Gly Lys Glu Gly Val
    450                 455                 460

Arg Gly Leu Ala Gly Pro Ile Gly Pro Pro Gly Glu Arg Gly Ala Ala
465                 470                 475                 480

Gly Leu Pro Gly Pro Lys Gly Glu Arg Gly Asp Gly Pro Lys Gly
                485                 490                 495

Ala Glu Gly Ala Pro Gly Lys Glu Gly Val Arg Gly Leu Ala Gly Pro
            500                 505                 510

Ile Gly Pro Pro Gly Pro Ala Gly Ala Pro Gly Ala Pro Gly Leu Gln
        515                 520                 525

Gly Met Pro Gly Glu Arg Gly Ala Ala Gly Leu Pro Gly Pro Lys Gly
    530                 535                 540

Glu Arg Gly Asp Gln Gly Pro Lys Gly Ala Glu Gly Ala Pro Gly Lys
545                 550                 555                 560

Glu Gly Val Arg Gly Leu Ala Gly Pro Ala Gly Ala Pro Gly Leu Gln
                565                 570                 575

Gly Ala Pro Gly Leu Gln Gly Met Pro Gly Glu Arg Gly Ala Ala Gly
            580                 585                 590

Leu Pro Gly Pro Lys Gly Glu Arg Gly Asp Val Gly Pro Lys Gly Ala
        595                 600                 605

Glu Gly Ala Pro Gly Ala Pro Gly Leu Gln Gly Met Pro Gly Glu Arg
    610                 615                 620

Gly Ala Ala Gly Leu Pro Gly Pro Lys Gly Glu Arg Gly Asp Lys Gly
625                 630                 635                 640

Pro Lys Gly Ala Glu Gly Ala Pro Gly Lys Glu Gly Val Arg Gly Leu
                645                 650                 655

Ala Gly Pro Ile Gly Pro Pro Gly Glu Arg Gly Ala Ala Gly Leu Pro
            660                 665                 670

Gly Pro Lys Gly Glu Arg Gly Asp Glu Gly Pro Lys Gly Ala Glu Gly
        675                 680                 685

Ala Pro Gly Lys Glu Gly Val Arg Gly Leu Ala Gly Pro Ile Gly Pro
    690                 695                 700

Pro Gly Pro Ala Gly Ala Pro Gly Ala Pro Gly Leu Gln Gly Met Pro
705                 710                 715                 720

Gly Glu Arg Gly Ala Ala Gly Leu Pro Gly Pro Lys Gly Glu Arg Gly
                725                 730                 735

Asp Gln Gly Pro Lys Gly Ala Glu Gly Ala Pro Gly Lys Glu Gly Val
            740                 745                 750

Arg Gly Leu Ala Gly Pro Ala Gly Gly
        755                 760

<210> SEQ ID NO 8
<211> LENGTH: 3535
<212> TYPE: PRT
<213> ORGANISM: Artificial
<220> FEATURE:
<223> OTHER INFORMATION: Sequence of plasmid pFFZalphaA

<400> SEQUENCE: 8

Ala Gly Ala Thr Cys Thr Ala Ala Cys Ala Thr Cys Cys Ala Ala Ala
1               5                   10                  15

Gly Ala Cys Gly Ala Ala Ala Gly Gly Thr Thr Gly Ala Ala Thr Gly
                20                  25                  30
```

```
Ala Ala Ala Cys Cys Thr Thr Thr Thr Gly Cys Cys Ala Thr Cys
            35                  40                  45
Cys Gly Ala Cys Ala Thr Cys Cys Ala Cys Ala Gly Gly Thr Cys Cys
    50                  55                  60
Ala Thr Thr Cys Thr Cys Ala Cys Ala Cys Ala Thr Ala Ala Gly Thr
65                  70                  75                  80
Gly Cys Cys Ala Ala Ala Cys Gly Cys Ala Ala Cys Ala Gly Gly Ala
                85                  90                  95
Gly Gly Gly Gly Ala Thr Ala Cys Ala Cys Thr Ala Gly Cys Ala Gly
                100                 105                 110
Cys Ala Gly Ala Cys Cys Gly Thr Thr Gly Cys Ala Ala Cys Gly
    115                 120                 125
Cys Ala Gly Gly Ala Cys Cys Thr Cys Ala Cys Thr Cys Cys Thr
    130                 135                 140
Cys Thr Thr Cys Thr Cys Cys Thr Ala Ala Cys Ala Cys Cys Cys
145                 150                 155                 160
Ala Cys Thr Thr Thr Thr Gly Cys Cys Ala Thr Cys Gly Ala Ala Ala
                165                 170                 175
Ala Ala Cys Cys Ala Gly Cys Cys Ala Gly Thr Thr Ala Thr Thr
                180                 185                 190
Gly Gly Gly Cys Thr Thr Gly Ala Thr Thr Gly Gly Ala Gly Cys Thr
                195                 200                 205
Cys Gly Cys Thr Cys Ala Thr Thr Cys Cys Ala Ala Thr Thr Cys Cys
    210                 215                 220
Thr Thr Cys Thr Ala Thr Thr Ala Gly Gly Cys Thr Ala Cys Thr Ala
225                 230                 235                 240
Ala Cys Ala Cys Cys Ala Thr Gly Ala Cys Thr Thr Ala Thr Thr
                245                 250                 255
Ala Gly Cys Cys Thr Gly Thr Cys Thr Ala Thr Cys Thr Cys Gly Gly
                260                 265                 270
Cys Cys Cys Cys Cys Thr Gly Gly Cys Gly Ala Gly Gly Thr Thr
    275                 280                 285
Cys Ala Thr Gly Thr Thr Thr Gly Thr Thr Ala Thr Thr Thr Cys
    290                 295                 300
Cys Gly Ala Ala Thr Gly Cys Ala Ala Cys Ala Ala Gly Cys Thr Cys
305                 310                 315                 320
Cys Gly Cys Ala Thr Thr Ala Cys Ala Cys Cys Gly Ala Ala Cys
                325                 330                 335
Ala Thr Cys Ala Cys Thr Cys Cys Ala Gly Ala Thr Gly Ala Gly Gly
                340                 345                 350
Gly Cys Thr Thr Thr Cys Thr Gly Ala Gly Thr Gly Thr Gly Gly Gly
                355                 360                 365
Gly Thr Cys Ala Ala Ala Thr Ala Gly Thr Thr Thr Cys Ala Thr Gly
                370                 375                 380
Thr Thr Cys Cys Cys Cys Ala Ala Ala Thr Gly Gly Cys Cys Cys Ala
385                 390                 395                 400
Ala Ala Ala Cys Thr Gly Ala Cys Ala Gly Thr Thr Ala Ala Ala
                405                 410                 415
Cys Gly Cys Thr Gly Thr Cys Thr Thr Gly Gly Ala Ala Cys Thr
    420                 425                 430
Ala Ala Thr Ala Thr Gly Ala Cys Ala Ala Ala Gly Cys Gly Thr
    435                 440                 445
Gly Ala Thr Cys Thr Cys Ala Thr Cys Cys Ala Ala Gly Ala Thr Gly
```

```
    450                 455                 460

Ala Ala Cys Thr Ala Ala Gly Thr Thr Thr Gly Gly Thr Thr Cys Gly
465                 470                 475                 480

Thr Thr Gly Ala Ala Ala Thr Gly Cys Thr Ala Ala Cys Gly Gly Cys
                485                 490                 495

Cys Ala Gly Thr Thr Gly Gly Thr Cys Ala Ala Ala Ala Ala Gly Ala
            500                 505                 510

Ala Ala Cys Thr Thr Cys Cys Ala Ala Ala Ala Gly Thr Cys Gly Gly
        515                 520                 525

Cys Ala Thr Ala Cys Cys Gly Thr Thr Thr Gly Thr Cys Thr Thr Gly
    530                 535                 540

Thr Thr Thr Gly Gly Thr Ala Thr Thr Gly Ala Thr Thr Gly Ala Cys
545                 550                 555                 560

Gly Ala Ala Thr Gly Cys Thr Cys Ala Ala Ala Ala Ala Thr Ala Ala
                565                 570                 575

Thr Cys Thr Cys Ala Thr Thr Ala Ala Thr Gly Cys Thr Thr Ala Gly
            580                 585                 590

Cys Gly Cys Ala Gly Thr Cys Thr Cys Thr Cys Thr Ala Thr Cys Gly
        595                 600                 605

Cys Thr Thr Cys Thr Gly Ala Ala Cys Cys Cys Cys Gly Gly Thr Gly
    610                 615                 620

Cys Ala Cys Cys Thr Gly Thr Gly Cys Cys Gly Ala Ala Ala Cys Gly
625                 630                 635                 640

Cys Ala Ala Ala Thr Gly Gly Gly Gly Ala Ala Ala Cys Ala Cys Cys
                645                 650                 655

Cys Gly Cys Thr Thr Thr Thr Thr Gly Gly Ala Thr Gly Ala Thr Thr
            660                 665                 670

Ala Thr Gly Cys Ala Thr Thr Gly Thr Cys Thr Cys Cys Ala Cys Ala
        675                 680                 685

Thr Thr Gly Thr Ala Thr Gly Cys Thr Thr Cys Cys Ala Ala Gly Ala
    690                 695                 700

Thr Thr Cys Thr Gly Gly Thr Gly Gly Gly Ala Ala Thr Ala Cys Thr
705                 710                 715                 720

Gly Cys Thr Gly Ala Thr Ala Gly Cys Cys Thr Ala Ala Cys Gly Thr
                725                 730                 735

Thr Cys Ala Thr Gly Ala Thr Cys Ala Ala Ala Ala Thr Thr Thr Ala
            740                 745                 750

Ala Cys Thr Gly Thr Thr Cys Thr Ala Ala Cys Cys Cys Cys Thr Ala
        755                 760                 765

Cys Thr Thr Gly Ala Cys Ala Gly Cys Ala Ala Thr Ala Thr Ala Thr
    770                 775                 780

Ala Ala Ala Cys Ala Gly Ala Ala Gly Gly Ala Ala Gly Cys Thr Gly
785                 790                 795                 800

Cys Cys Cys Thr Gly Thr Cys Thr Thr Ala Ala Ala Cys Cys Thr Thr
                805                 810                 815

Thr Thr Thr Thr Thr Thr Thr Ala Thr Cys Ala Thr Cys Ala Thr Thr
            820                 825                 830

Ala Thr Thr Ala Gly Cys Thr Thr Ala Cys Thr Thr Thr Cys Ala Thr
        835                 840                 845

Ala Ala Thr Thr Gly Cys Gly Ala Cys Thr Gly Gly Thr Thr Cys Cys
    850                 855                 860

Ala Ala Thr Thr Gly Ala Cys Ala Ala Gly Cys Thr Thr Thr Thr Gly
865                 870                 875                 880
```

-continued

```
Ala Thr Thr Thr Thr Ala Ala Cys Gly Ala Cys Thr Thr Thr Thr Ala
                885                 890                 895
Ala Cys Gly Ala Cys Ala Ala Cys Thr Thr Gly Ala Gly Ala Ala Gly
            900                 905                 910

Ala Thr Cys Ala Ala Ala Ala Ala Ala Cys Ala Ala Cys Thr Ala Ala
        915                 920                 925

Thr Thr Ala Thr Thr Cys Gly Ala Ala Ala Cys Gly Ala Thr Gly Ala
    930                 935                 940

Gly Ala Thr Thr Thr Cys Cys Thr Thr Cys Ala Ala Thr Thr Thr Thr
945                 950                 955                 960

Thr Ala Cys Thr Gly Cys Thr Gly Thr Thr Thr Thr Ala Thr Thr Cys
                965                 970                 975

Gly Cys Ala Gly Cys Ala Thr Cys Cys Thr Cys Cys Gly Cys Ala Thr
            980                 985                 990

Thr Ala Gly Cys Thr Gly Cys Thr  Cys Cys Ala Gly Thr  Cys Ala Ala
        995                 1000                1005

Cys Ala  Cys Thr Ala Cys Ala  Ala Cys Ala Gly Ala  Ala Gly Ala
    1010                1015                1020

Thr Gly  Ala Ala Ala Cys Gly  Gly Cys Ala Cys Ala  Ala Ala Thr
    1025                1030                1035

Thr Cys  Cys Gly Gly Cys Thr  Gly Ala Ala Gly Cys  Thr Gly Thr
    1040                1045                1050

Cys Ala  Thr Cys Gly Gly Thr  Thr Ala Cys Thr Cys  Ala Gly Ala
    1055                1060                1065

Thr Thr  Thr Ala Gly Ala Ala  Gly Gly Gly Gly Ala  Thr Thr Thr
    1070                1075                1080

Cys Gly  Ala Thr Gly Thr Thr  Gly Cys Thr Gly Thr  Thr Thr Thr
    1085                1090                1095

Gly Cys  Cys Ala Thr Thr Thr  Thr Cys Cys Ala Ala  Cys Ala Gly
    1100                1105                1110

Cys Ala  Cys Ala Ala Ala Thr  Ala Ala Cys Gly Gly  Gly Thr Thr
    1115                1120                1125

Ala Thr  Thr Gly Thr Thr Thr  Ala Thr Ala Ala Ala  Thr Ala Cys
    1130                1135                1140

Thr Ala  Cys Thr Ala Thr Thr  Gly Cys Cys Ala Gly  Cys Ala Thr
    1145                1150                1155

Thr Gly  Cys Thr Gly Cys Thr  Ala Ala Ala Gly Ala  Ala Gly Ala
    1160                1165                1170

Ala Gly  Gly Gly Gly Thr Ala  Thr Cys Thr Cys Thr  Cys Gly Ala
    1175                1180                1185

Gly Ala  Ala Ala Ala Gly Ala  Gly Ala Gly Gly Cys  Thr Gly Ala
    1190                1195                1200

Ala Gly  Cys Thr Gly Ala Ala  Thr Thr Cys Ala Cys  Gly Thr Gly
    1205                1210                1215

Gly Cys  Cys Cys Ala Gly Cys  Cys Gly Gly Cys Cys  Gly Thr Cys
    1220                1225                1230

Thr Cys  Gly Gly Ala Thr Cys  Gly Gly Thr Ala Cys  Cys Ala Gly
    1235                1240                1245

Cys Cys  Gly Cys Gly Gly Cys  Gly Gly Cys Cys Gly  Cys Cys Ala
    1250                1255                1260

Gly Cys  Thr Thr Thr Cys Thr  Ala Gly Ala Gly Thr  Cys Gly Ala
    1265                1270                1275
```

```
Cys Thr Gly Ala Gly Thr Thr Thr Gly Thr Ala Gly Cys Cys Thr
    1280                1285                1290

Thr Ala Gly Ala Cys Ala Thr Gly Ala Cys Thr Gly Thr Thr Cys
    1295                1300                1305

Cys Thr Cys Ala Gly Thr Thr Cys Ala Ala Gly Thr Thr Gly Gly
    1310                1315                1320

Gly Cys Ala Cys Thr Thr Ala Cys Gly Ala Gly Ala Ala Gly Ala
    1325                1330                1335

Cys Cys Gly Gly Thr Cys Thr Thr Gly Cys Thr Ala Gly Ala Thr
    1340                1345                1350

Thr Cys Thr Ala Ala Thr Cys Ala Ala Gly Ala Gly Gly Ala Thr
    1355                1360                1365

Gly Thr Cys Ala Gly Ala Ala Thr Gly Cys Cys Ala Thr Thr Thr
    1370                1375                1380

Gly Cys Cys Thr Gly Ala Gly Ala Gly Ala Thr Gly Cys Ala Gly
    1385                1390                1395

Gly Cys Thr Thr Cys Ala Thr Thr Thr Thr Gly Ala Thr Ala
    1400                1405                1410

Cys Thr Thr Thr Thr Thr Thr Ala Thr Thr Thr Gly Thr Ala Ala
    1415                1420                1425

Cys Cys Thr Ala Thr Ala Thr Ala Gly Thr Ala Thr Ala Gly Gly
    1430                1435                1440

Ala Thr Thr Thr Thr Thr Thr Thr Gly Thr Cys Ala Thr Thr
    1445                1450                1455

Thr Thr Gly Thr Thr Thr Cys Thr Thr Cys Thr Cys Gly Thr Ala
    1460                1465                1470

Cys Gly Ala Gly Cys Thr Thr Gly Cys Thr Cys Thr Gly Thr Ala
    1475                1480                1485

Thr Cys Ala Gly Cys Cys Thr Ala Thr Cys Thr Cys Gly Cys Ala
    1490                1495                1500

Gly Cys Thr Gly Ala Thr Gly Ala Ala Thr Ala Thr Cys Thr Thr
    1505                1510                1515

Gly Thr Gly Gly Thr Ala Gly Gly Gly Thr Thr Thr Gly Gly
    1520                1525                1530

Gly Ala Ala Ala Ala Thr Cys Ala Thr Thr Cys Gly Ala Gly Thr
    1535                1540                1545

Thr Thr Gly Ala Thr Gly Thr Thr Thr Thr Thr Cys Thr Thr Gly
    1550                1555                1560

Gly Thr Ala Thr Thr Thr Cys Cys Cys Ala Cys Thr Cys Cys Thr
    1565                1570                1575

Cys Thr Thr Cys Ala Gly Ala Gly Thr Ala Cys Ala Gly Ala Ala
    1580                1585                1590

Gly Ala Thr Thr Ala Ala Gly Thr Gly Ala Gly Ala Cys Cys Thr
    1595                1600                1605

Thr Cys Gly Thr Thr Thr Gly Thr Gly Cys Ala Cys Thr Ala Gly
    1610                1615                1620

Thr Cys Cys Cys Ala Cys Ala Cys Ala Cys Cys Ala Thr Ala Gly
    1625                1630                1635

Cys Thr Thr Cys Ala Ala Ala Ala Thr Gly Thr Thr Thr Cys Thr
    1640                1645                1650

Ala Cys Thr Cys Cys Thr Thr Thr Thr Thr Ala Cys Thr Cys
    1655                1660                1665

Thr Thr Cys Cys Ala Gly Ala Thr Thr Thr Thr Cys Thr Cys Gly
```

-continued

```
            1670                1675                1680
Gly Ala Cys Thr Cys Cys Gly Cys Gly Cys Ala Thr Cys Gly Cys
    1685                1690                1695
Cys Gly Thr Ala Cys Ala Cys Thr Thr Cys Ala Ala Ala Ala Ala
    1700                1705                1710
Cys Ala Cys Cys Cys Ala Ala Gly Cys Ala Cys Ala Gly Cys Ala
    1715                1720                1725
Thr Ala Cys Thr Ala Ala Ala Thr Thr Thr Thr Cys Cys Cys Thr
    1730                1735                1740
Cys Thr Thr Thr Cys Thr Thr Cys Cys Thr Cys Thr Ala Gly Gly
    1745                1750                1755
Gly Thr Gly Thr Cys Gly Thr Thr Ala Ala Thr Ala Cys Cys
    1760                1765                1770
Cys Gly Thr Ala Cys Thr Ala Ala Ala Gly Gly Thr Thr Thr Gly
    1775                1780                1785
Gly Ala Ala Ala Ala Gly Ala Ala Ala Ala Ala Gly Ala Gly
    1790                1795                1800
Ala Cys Cys Gly Cys Cys Thr Cys Gly Thr Thr Cys Thr Thr
    1805                1810                1815
Thr Thr Thr Cys Thr Thr Cys Gly Thr Cys Gly Ala Ala Ala Ala
    1820                1825                1830
Ala Gly Gly Cys Ala Ala Thr Ala Ala Ala Ala Ala Thr Thr Thr
    1835                1840                1845
Thr Thr Ala Thr Cys Ala Cys Gly Thr Thr Thr Cys Thr Thr Thr
    1850                1855                1860
Thr Thr Cys Thr Thr Gly Ala Ala Ala Thr Thr Thr Thr Thr Thr
    1865                1870                1875
Thr Thr Thr Thr Thr Ala Gly Thr Thr Thr Thr Thr Thr Thr Cys
    1880                1885                1890
Thr Cys Thr Thr Thr Cys Ala Gly Thr Gly Ala Cys Cys Thr Cys
    1895                1900                1905
Cys Ala Thr Thr Gly Ala Thr Ala Thr Thr Ala Ala Gly Thr
    1910                1915                1920
Thr Ala Ala Thr Ala Ala Ala Cys Gly Gly Thr Cys Thr Thr Cys
    1925                1930                1935
Ala Ala Thr Thr Thr Cys Thr Cys Ala Ala Gly Thr Thr Thr Cys
    1940                1945                1950
Ala Gly Thr Thr Thr Cys Ala Thr Thr Thr Thr Cys Thr Thr
    1955                1960                1965
Gly Thr Thr Cys Thr Ala Thr Thr Ala Cys Ala Ala Cys Thr Thr
    1970                1975                1980
Thr Thr Thr Thr Thr Ala Cys Thr Thr Cys Thr Thr Gly Thr Thr
    1985                1990                1995
Cys Ala Thr Thr Ala Gly Ala Ala Ala Gly Ala Ala Ala Gly Cys
    2000                2005                2010
Ala Thr Ala Gly Cys Ala Ala Thr Cys Thr Ala Ala Thr Cys Thr
    2015                2020                2025
Ala Ala Gly Gly Gly Gly Cys Gly Gly Thr Gly Thr Thr Gly Ala
    2030                2035                2040
Cys Ala Ala Thr Thr Ala Ala Thr Cys Ala Thr Cys Gly Gly Cys
    2045                2050                2055
Ala Thr Ala Gly Thr Ala Thr Ala Thr Cys Gly Gly Cys Ala Thr
    2060                2065                2070
```

-continued

```
Ala Gly Thr Ala Thr Ala Ala Thr Ala Cys Gly Ala  Cys Ala Ala
    2075                2080                2085
Gly Gly Thr Gly Ala Gly Gly Ala Ala Cys Thr Ala  Ala Ala Cys
    2090                2095                2100
Cys Ala Thr Gly Gly Cys Cys Ala Ala Gly Thr Thr  Gly Ala Cys
    2105                2110                2115
Cys Ala Gly Thr Gly Cys Cys Gly Thr Thr Cys Cys  Gly Gly Thr
    2120                2125                2130
Gly Cys Thr Cys Ala Cys Cys Gly Cys Gly Cys Gly  Cys Gly Ala
    2135                2140                2145
Cys Gly Thr Cys Gly Cys Cys Gly Gly Ala Gly Cys  Gly Gly Thr
    2150                2155                2160
Cys Gly Ala Gly Thr Thr Cys Thr Gly Gly Ala Cys  Cys Gly Ala
    2165                2170                2175
Cys Cys Gly Gly Cys Thr Cys Gly Gly Gly Thr Thr  Cys Thr Cys
    2180                2185                2190
Cys Cys Gly Cys Gly Ala Cys Thr Thr Cys Gly Thr  Gly Gly Ala
    2195                2200                2205
Gly Gly Ala Cys Gly Ala Cys Thr Thr Cys Gly Cys  Cys Gly Gly
    2210                2215                2220
Thr Gly Thr Gly Gly Thr Cys Cys Gly Gly Gly Ala  Cys Gly Ala
    2225                2230                2235
Cys Gly Thr Gly Ala Cys Cys Cys Thr Gly Thr Thr  Cys Ala Thr
    2240                2245                2250
Cys Ala Gly Cys Gly Cys Gly Gly Thr Cys Ala Gly  Gly Gly Ala
    2255                2260                2265
Cys Cys Ala Gly Gly Thr Gly Gly Thr Gly Cys Cys  Gly Gly Ala
    2270                2275                2280
Cys Ala Ala Cys Ala Cys Cys Thr Gly Gly Cys Cys  Cys Thr Gly
    2285                2290                2295
Gly Gly Thr Gly Thr Gly Gly Gly Thr Gly Cys Gly  Cys Gly Gly
    2300                2305                2310
Cys Cys Thr Gly Gly Ala Cys Gly Ala Gly Cys Thr  Gly Thr Ala
    2315                2320                2325
Cys Gly Cys Cys Gly Ala Gly Thr Gly Gly Thr Cys  Gly Gly Ala
    2330                2335                2340
Gly Gly Thr Cys Gly Thr Gly Thr Cys Cys Ala Cys  Gly Ala Ala
    2345                2350                2355
Cys Thr Thr Cys Cys Gly Gly Gly Ala Cys Gly Cys  Cys Thr Cys
    2360                2365                2370
Cys Gly Gly Gly Cys Cys Gly Gly Cys Cys Ala Thr  Gly Ala Cys
    2375                2380                2385
Cys Gly Ala Gly Ala Thr Cys Gly Gly Cys Gly Ala  Gly Cys Ala
    2390                2395                2400
Gly Cys Cys Gly Thr Gly Gly Gly Gly Cys Gly  Gly Gly Ala
    2405                2410                2415
Gly Thr Thr Cys Gly Cys Cys Thr Gly Cys Gly  Cys Gly Ala
    2420                2425                2430
Cys Cys Cys Gly Gly Cys Cys Gly Gly Cys Ala Ala  Cys Thr Gly
    2435                2440                2445
Cys Gly Thr Gly Cys Ala Cys Thr Thr Cys Gly Thr  Cys Gly Cys
    2450                2455                2460
```

```
Cys Gly Ala Gly Gly Ala Gly Cys Ala Gly Gly Ala Cys Thr Gly
    2465                2470                2475
Ala Cys Ala Cys Gly Thr Cys Cys Gly Ala Cys Gly Gly Cys Gly
    2480                2485                2490
Gly Cys Cys Cys Ala Cys Gly Gly Gly Thr Cys Cys Cys Ala Gly
    2495                2500                2505
Gly Cys Cys Thr Cys Gly Gly Ala Gly Ala Thr Cys Cys Gly Thr
    2510                2515                2520
Cys Cys Cys Cys Cys Thr Thr Thr Thr Cys Cys Thr Thr Thr Gly
    2525                2530                2535
Thr Cys Gly Ala Thr Ala Thr Cys Ala Thr Gly Thr Ala Ala Thr
    2540                2545                2550
Thr Ala Gly Thr Thr Ala Thr Gly Thr Cys Ala Cys Gly Cys Thr
    2555                2560                2565
Thr Ala Cys Ala Thr Thr Cys Ala Cys Gly Cys Cys Cys Thr Cys
    2570                2575                2580
Cys Cys Cys Cys Cys Ala Cys Ala Thr Cys Cys Gly Cys Thr Cys
    2585                2590                2595
Thr Ala Ala Cys Cys Gly Ala Ala Ala Gly Gly Ala Ala Gly Gly
    2600                2605                2610
Gly Ala Gly Thr Thr Ala Gly Ala Cys Ala Ala Cys Cys Thr Gly
    2615                2620                2625
Ala Ala Gly Thr Cys Thr Ala Gly Gly Thr Cys Cys Cys Thr Ala
    2630                2635                2640
Thr Thr Thr Ala Thr Thr Thr Thr Thr Thr Thr Ala Thr Ala Gly
    2645                2650                2655
Thr Thr Ala Thr Gly Thr Thr Ala Gly Thr Ala Thr Thr Ala Ala
    2660                2665                2670
Gly Ala Ala Cys Gly Thr Thr Ala Thr Thr Thr Ala Thr Ala Thr
    2675                2680                2685
Thr Thr Cys Ala Ala Ala Thr Thr Thr Thr Cys Thr Thr Thr Thr
    2690                2695                2700
Thr Thr Thr Thr Thr Cys Thr Gly Thr Ala Cys Ala Gly Ala Cys
    2705                2710                2715
Gly Cys Gly Thr Gly Thr Ala Cys Gly Cys Ala Thr Gly Thr Ala
    2720                2725                2730
Ala Cys Ala Thr Thr Ala Thr Ala Cys Thr Gly Ala Ala Ala Ala
    2735                2740                2745
Cys Cys Thr Thr Gly Cys Thr Thr Gly Ala Gly Ala Ala Gly Gly
    2750                2755                2760
Thr Thr Thr Gly Gly Gly Ala Cys Gly Cys Thr Cys Gly Ala
    2765                2770                2775
Ala Gly Gly Cys Thr Thr Thr Ala Ala Thr Thr Thr Gly Cys Ala
    2780                2785                2790
Ala Gly Cys Thr Gly Gly Ala Gly Ala Cys Cys Ala Ala Cys Ala
    2795                2800                2805
Thr Gly Thr Gly Ala Gly Cys Ala Ala Ala Gly Gly Cys Cys
    2810                2815                2820
Ala Gly Cys Ala Ala Ala Ala Gly Gly Cys Cys Ala Gly Gly Ala
    2825                2830                2835
Ala Cys Cys Gly Thr Ala Ala Ala Ala Ala Gly Gly Cys Cys Gly
    2840                2845                2850
Cys Gly Thr Thr Gly Cys Thr Gly Gly Cys Gly Thr Thr Thr Thr
```

```
                  2855                2860                2865

Thr Cys Cys Ala Thr Ala Gly Gly Cys Thr Cys  Gly Cys Cys
        2870                2875                2880

Cys Cys Cys Cys Thr Gly Ala Cys Gly Ala Gly  Cys Ala Thr Cys
        2885                2890                2895

Ala Cys Ala Ala Ala Ala Thr Cys Gly Ala Cys  Gly Cys Thr
        2900                2905                2910

Cys Ala Ala Gly Thr Cys Ala Gly Ala Gly Gly  Thr Gly Gly Cys
        2915                2920                2925

Gly Ala Ala Ala Cys Cys Cys Gly Ala Cys Ala  Gly Gly Ala Cys
        2930                2935                2940

Thr Ala Thr Ala Ala Ala Gly Ala Thr Ala Cys  Cys Ala Gly Gly
        2945                2950                2955

Cys Gly Thr Thr Thr Cys Cys Cys Cys Thr Gly  Gly Ala Ala
        2960                2965                2970

Gly Cys Thr Cys Cys Cys Thr Cys Gly Thr Gly  Cys Gly Cys Thr
        2975                2980                2985

Cys Thr Cys Cys Thr Gly Thr Thr Cys Cys Gly  Ala Cys Cys Cys
        2990                2995                3000

Thr Gly Cys Cys Gly Cys Thr Thr Ala Cys Cys  Gly Gly Ala Thr
        3005                3010                3015

Ala Cys Cys Thr Gly Thr Cys Cys Gly Cys Cys  Thr Thr Thr Cys
        3020                3025                3030

Thr Cys Cys Cys Thr Thr Cys Gly Gly Gly Ala  Ala Gly Cys Gly
        3035                3040                3045

Thr Gly Gly Cys Gly Cys Thr Thr Thr Cys Thr  Cys Ala Ala Thr
        3050                3055                3060

Gly Cys Thr Cys Ala Cys Gly Cys Thr Gly Thr  Ala Gly Gly Thr
        3065                3070                3075

Ala Thr Cys Thr Cys Ala Gly Thr Thr Cys Gly  Gly Thr Gly Thr
        3080                3085                3090

Ala Gly Gly Thr Cys Gly Thr Thr Cys Gly Cys  Thr Cys Cys Ala
        3095                3100                3105

Ala Gly Cys Thr Gly Gly Gly Cys Thr Gly Thr  Gly Thr Gly Cys
        3110                3115                3120

Ala Cys Gly Ala Ala Cys Cys Cys Cys Cys Gly  Thr Thr Cys
        3125                3130                3135

Ala Gly Cys Cys Cys Gly Ala Cys Cys Gly Cys  Thr Gly Cys Gly
        3140                3145                3150

Cys Cys Thr Thr Ala Thr Cys Cys Gly Gly Thr  Ala Ala Cys Thr
        3155                3160                3165

Ala Thr Cys Gly Thr Cys Thr Thr Gly Ala Gly  Thr Cys Cys Ala
        3170                3175                3180

Ala Cys Cys Cys Gly Gly Thr Ala Ala Gly Ala  Cys Ala Cys Gly
        3185                3190                3195

Ala Cys Thr Thr Ala Thr Cys Gly Cys Cys Ala  Cys Thr Gly Gly
        3200                3205                3210

Cys Ala Gly Cys Ala Gly Cys Cys Ala Cys Thr  Gly Gly Thr Ala
        3215                3220                3225

Ala Cys Ala Gly Gly Ala Thr Thr Ala Gly Cys  Ala Gly Ala Gly
        3230                3235                3240

Cys Gly Ala Gly Gly Thr Ala Thr Gly Thr Ala  Gly Gly Cys Gly
        3245                3250                3255
```

Gly Thr Gly Cys Thr Ala Cys Ala Gly Ala Gly Thr Thr Cys Thr
         3260                3265                3270

Thr Gly Ala Ala Gly Thr Gly Gly Thr Gly Gly Cys Cys Thr Ala
         3275                3280                3285

Ala Cys Thr Ala Cys Gly Gly Cys Thr Ala Cys Ala Cys Thr Ala
         3290                3295                3300

Gly Ala Ala Gly Gly Ala Cys Ala Gly Thr Ala Thr Thr Thr Gly
         3305                3310                3315

Gly Thr Ala Thr Cys Thr Gly Cys Gly Cys Thr Gly Cys Thr Gly Cys
         3320                3325                3330

Thr Gly Ala Ala Gly Cys Cys Ala Gly Thr Ala Cys Cys Thr
         3335                3340                3345

Thr Cys Gly Gly Ala Ala Ala Ala Gly Ala Gly Thr Thr Gly
         3350                3355                3360

Gly Thr Ala Gly Cys Thr Cys Thr Thr Gly Ala Thr Cys Cys Gly
         3365                3370                3375

Gly Cys Ala Ala Cys Ala Ala Cys Cys Ala Cys Cys Gly
         3380                3385                3390

Cys Thr Gly Gly Thr Ala Gly Cys Gly Gly Thr Gly Gly Thr Thr
         3395                3400                3405

Thr Thr Thr Thr Thr Gly Thr Thr Thr Gly Cys Ala Ala Gly Cys
         3410                3415                3420

Ala Gly Cys Ala Gly Ala Thr Thr Ala Cys Gly Cys Gly Cys Ala
         3425                3430                3435

Gly Ala Ala Ala Ala Ala Ala Gly Gly Ala Thr Cys Thr Cys
         3440                3445                3450

Ala Ala Gly Ala Ala Gly Ala Thr Cys Cys Thr Thr Thr Gly Ala
         3455                3460                3465

Thr Cys Thr Thr Thr Thr Cys Thr Ala Cys Gly Gly Gly Gly Thr
         3470                3475                3480

Cys Thr Gly Ala Cys Gly Cys Thr Cys Ala Gly Thr Gly Gly Ala
         3485                3490                3495

Ala Cys Gly Ala Ala Ala Ala Cys Thr Cys Ala Cys Gly Thr Thr
         3500                3505                3510

Ala Ala Gly Gly Gly Ala Thr Thr Thr Thr Gly Gly Thr Cys Ala
         3515                3520                3525

Thr Gly Ala Gly Ala Thr Cys
         3530                3535

<210> SEQ ID NO 9
<211> LENGTH: 572
<212> TYPE: PRT
<213> ORGANISM: Artificial
<220> FEATURE:
<223> OTHER INFORMATION: Sequence of ICP3 varient 1

<400> SEQUENCE: 9

Gly Pro Pro Gly Ala Pro Gly Leu Gln Gly Ala Pro Gly Leu Gln Gly
1               5                   10                  15

Met Pro Gly Glu Arg Gly Ala Ala Gly Leu Pro Gly Pro Lys Gly Glu
            20                  25                  30

Arg Gly Asp Val Gly Pro Lys Gly Ala Glu Gly Ala Pro Gly Ala Pro
        35                  40                  45

Gly Leu Gln Gly Met Pro Gly Glu Arg Gly Ala Ala Gly Leu Pro Gly
    50                  55                  60

```
Pro Lys Gly Glu Arg Gly Asp Lys Gly Pro Lys Gly Ala Glu Gly Ala
 65                  70                  75                  80

Pro Gly Lys Glu Gly Val Arg Gly Leu Pro Gly Pro Ile Gly Pro Pro
                 85                  90                  95

Gly Glu Arg Gly Ala Ala Gly Leu Pro Gly Pro Lys Gly Glu Arg Gly
            100                 105                 110

Asp Glu Gly Pro Lys Gly Ala Glu Gly Ala Pro Gly Lys Glu Gly Val
            115                 120                 125

Arg Gly Leu Gln Gly Pro Ile Gly Pro Pro Gly Pro Ala Gly Ala Pro
            130                 135                 140

Gly Ala Pro Gly Leu Gln Gly Met Pro Gly Glu Arg Gly Ala Ala Gly
145                 150                 155                 160

Leu Pro Gly Pro Lys Gly Glu Arg Gly Asp Gln Gly Pro Lys Gly Ala
                165                 170                 175

Glu Gly Ala Pro Gly Lys Glu Gly Val Arg Gly Leu Pro Gly Pro Ala
            180                 185                 190

Gly Ala Pro Gly Leu Gln Gly Ala Pro Gly Leu Gln Gly Met Pro Gly
            195                 200                 205

Glu Arg Gly Ala Ala Gly Leu Pro Gly Pro Lys Gly Glu Arg Gly Asp
210                 215                 220

Val Gly Pro Lys Gly Ala Glu Gly Ala Pro Gly Ala Pro Gly Leu Gln
225                 230                 235                 240

Gly Met Pro Gly Glu Arg Gly Ala Ala Gly Leu Pro Gly Pro Lys Gly
                245                 250                 255

Glu Arg Gly Asp Lys Gly Pro Lys Gly Ala Glu Gly Ala Pro Gly Lys
            260                 265                 270

Glu Gly Val Arg Gly Leu Pro Gly Pro Ile Gly Pro Pro Gly Glu Arg
            275                 280                 285

Gly Ala Ala Gly Leu Pro Gly Pro Lys Gly Glu Arg Gly Asp Glu Gly
            290                 295                 300

Pro Lys Gly Ala Glu Gly Ala Pro Gly Lys Glu Gly Val Arg Gly Leu
305                 310                 315                 320

Gln Gly Pro Ile Gly Pro Pro Gly Pro Ala Gly Ala Pro Gly Ala Pro
                325                 330                 335

Gly Leu Gln Gly Met Pro Gly Glu Arg Gly Ala Ala Gly Leu Pro Gly
            340                 345                 350

Pro Lys Gly Glu Arg Gly Asp Gln Gly Pro Lys Gly Ala Glu Gly Ala
            355                 360                 365

Pro Gly Lys Glu Gly Val Arg Gly Leu Pro Gly Pro Ala Gly Ala Pro
            370                 375                 380

Gly Leu Gln Gly Ala Pro Gly Leu Gln Gly Met Pro Gly Glu Arg Gly
385                 390                 395                 400

Ala Ala Gly Leu Pro Gly Pro Lys Gly Glu Arg Gly Asp Val Gly Pro
                405                 410                 415

Lys Gly Ala Glu Gly Ala Pro Gly Ala Pro Gly Leu Gln Gly Met Pro
            420                 425                 430

Gly Glu Arg Gly Ala Ala Gly Leu Pro Gly Pro Lys Gly Glu Arg Gly
            435                 440                 445

Asp Lys Gly Pro Lys Gly Ala Glu Gly Ala Pro Gly Lys Glu Gly Val
            450                 455                 460

Arg Gly Leu Pro Gly Pro Ile Gly Pro Pro Gly Glu Arg Gly Ala Ala
465                 470                 475                 480
```

```
Gly Leu Pro Gly Pro Lys Gly Glu Arg Gly Asp Glu Gly Pro Lys Gly
                485                 490                 495
Ala Glu Gly Ala Pro Gly Lys Glu Gly Val Arg Gly Leu Gln Gly Pro
            500                 505                 510
Ile Gly Pro Pro Gly Pro Ala Gly Ala Pro Gly Ala Pro Gly Leu Gln
            515                 520                 525
Gly Met Pro Gly Glu Arg Gly Ala Ala Gly Leu Pro Gly Pro Lys Gly
            530                 535                 540
Glu Arg Gly Asp Gln Gly Pro Lys Gly Ala Glu Gly Ala Pro Gly Lys
545                 550                 555                 560
Glu Gly Val Arg Gly Leu Pro Gly Pro Ala Gly Gly
                565                 570
```

\<210\> SEQ ID NO 10
\<211\> LENGTH: 572
\<212\> TYPE: PRT
\<213\> ORGANISM: Artificial
\<220\> FEATURE:
\<223\> OTHER INFORMATION: Sequence of ICP3 variant 2

\<400\> SEQUENCE: 10

```
Gly Pro Pro Gly Ala Pro Gly Leu Gln Gly Ala Pro Gly Leu Gln Gly
1               5                   10                  15
Met Pro Gly Glu Arg Gly Ala Ala Gly Leu Pro Gly Pro Lys Gly Gln
            20                  25                  30
Arg Gly Asp Val Gly Pro Lys Gly Ala Glu Gly Ala Pro Gly Ala Pro
            35                  40                  45
Gly Leu Gln Gly Met Pro Gly Glu Arg Gly Ala Ala Gly Leu Pro Gly
        50                  55                  60
Pro Lys Gly Glu Arg Gly Asp Lys Gly Pro Lys Gly Ala Glu Gly Ala
65                  70                  75                  80
Pro Gly Lys Glu Gly Val Arg Gly Leu Pro Gly Pro Ile Gly Pro Pro
                85                  90                  95
Gly Glu Arg Gly Ala Ala Gly Leu Pro Gly Pro Lys Gly Glu Arg Gly
            100                 105                 110
Asp Lys Gly Pro Lys Gly Ala Glu Gly Ala Pro Gly Lys Glu Gly Val
            115                 120                 125
Arg Gly Leu Gln Gly Pro Ile Gly Pro Pro Gly Pro Ala Gly Ala Pro
        130                 135                 140
Gly Ala Pro Gly Leu Gln Gly Met Pro Gly Glu Arg Gly Ala Ala Gly
145                 150                 155                 160
Leu Pro Gly Pro Lys Gly Gln Arg Gly Asp Val Gly Pro Lys Gly Ala
                165                 170                 175
Glu Gly Ala Pro Gly Lys Glu Gly Val Arg Gly Leu Pro Gly Pro Ala
            180                 185                 190
Gly Ala Pro Gly Leu Gln Gly Ala Pro Gly Leu Gln Gly Met Pro Gly
            195                 200                 205
Glu Arg Gly Ala Ala Gly Leu Pro Gly Pro Lys Gly Gln Arg Gly Asp
        210                 215                 220
Val Gly Pro Lys Gly Ala Glu Gly Ala Pro Gly Ala Pro Gly Leu Gln
225                 230                 235                 240
Gly Met Pro Gly Glu Arg Gly Ala Ala Gly Leu Pro Gly Pro Lys Gly
                245                 250                 255
Glu Arg Gly Asp Lys Gly Pro Lys Gly Ala Glu Gly Ala Pro Gly Lys
            260                 265                 270
```

-continued

```
Glu Gly Val Arg Gly Leu Pro Gly Pro Ile Gly Pro Pro Gly Glu Arg
                275                 280                 285

Gly Ala Ala Gly Leu Pro Gly Pro Lys Gly Glu Arg Gly Asp Lys Gly
            290                 295                 300

Pro Lys Gly Ala Glu Gly Ala Pro Gly Lys Glu Gly Val Arg Gly Leu
305                 310                 315                 320

Gln Gly Pro Ile Gly Pro Pro Gly Ala Gly Ala Pro Gly Ala Pro
                325                 330                 335

Gly Leu Gln Gly Met Pro Gly Glu Arg Gly Ala Ala Gly Leu Pro Gly
            340                 345                 350

Pro Lys Gly Gln Arg Gly Asp Val Gly Pro Lys Gly Ala Glu Gly Ala
            355                 360                 365

Pro Gly Lys Glu Gly Val Arg Gly Leu Pro Gly Pro Ala Gly Ala Pro
            370                 375                 380

Gly Leu Gln Gly Ala Pro Gly Leu Gln Gly Met Pro Gly Glu Arg Gly
385                 390                 395                 400

Ala Ala Gly Leu Pro Gly Pro Lys Gly Gln Arg Gly Asp Val Gly Pro
                405                 410                 415

Lys Gly Ala Glu Gly Ala Pro Gly Ala Pro Gly Leu Gln Gly Met Pro
            420                 425                 430

Gly Glu Arg Gly Ala Ala Gly Leu Pro Gly Pro Lys Gly Glu Arg Gly
        435                 440                 445

Asp Lys Gly Pro Lys Gly Ala Glu Gly Ala Pro Gly Lys Glu Gly Val
        450                 455                 460

Arg Gly Leu Pro Gly Pro Ile Gly Pro Pro Gly Glu Arg Gly Ala Ala
465                 470                 475                 480

Gly Leu Pro Gly Pro Lys Gly Glu Arg Gly Asp Lys Gly Pro Lys Gly
                485                 490                 495

Ala Glu Gly Ala Pro Gly Lys Glu Gly Val Arg Gly Leu Gln Gly Pro
            500                 505                 510

Ile Gly Pro Pro Gly Pro Ala Gly Ala Pro Gly Ala Pro Gly Leu Gln
        515                 520                 525

Gly Met Pro Gly Glu Arg Gly Ala Ala Gly Leu Pro Gly Pro Lys Gly
        530                 535                 540

Gln Arg Gly Asp Val Gly Pro Lys Gly Ala Glu Gly Ala Pro Gly Lys
545                 550                 555                 560

Glu Gly Val Arg Gly Leu Pro Gly Pro Ala Gly Gly
                565                 570
```

<210> SEQ ID NO 11
<211> LENGTH: 572
<212> TYPE: PRT
<213> ORGANISM: Artificial
<220> FEATURE:
<223> OTHER INFORMATION: Sequence of ICP3 variant 3

<400> SEQUENCE: 11

```
Gly Pro Pro Gly Ala Pro Gly Leu Gln Gly Ala Pro Gly Leu Gln Gly
1               5                   10                  15

Met Pro Gly Glu Arg Gly Ala Ala Gly Leu Pro Gly Pro Lys Gly Gln
            20                  25                  30

Arg Gly Asp Asn Gly Pro Lys Gly Ala Glu Gly Ala Pro Gly Ala Pro
        35                  40                  45

Gly Leu Gln Gly Met Pro Gly Glu Arg Gly Ala Ala Gly Leu Pro Gly
    50                  55                  60
```

```
Pro Lys Gly Asn Arg Gly Asp Lys Gly Pro Lys Gly Ala Glu Gly Ala
 65                  70                  75                  80

Pro Gly Lys Glu Gly Val Arg Gly Leu Pro Gly Pro Ile Gly Pro Pro
                 85                  90                  95

Gly Glu Arg Gly Ala Ala Gly Leu Pro Gly Pro Lys Gly Asn Arg Gly
            100                 105                 110

Asp Glu Gly Pro Lys Gly Ala Glu Gly Ala Pro Gly Lys Glu Gly Val
        115                 120                 125

Arg Gly Leu Gln Gly Pro Ile Gly Pro Pro Gly Pro Ala Gly Ala Pro
130                 135                 140

Gly Ala Pro Gly Leu Gln Gly Met Pro Gly Glu Arg Gly Ala Ala Gly
145                 150                 155                 160

Leu Pro Gly Pro Lys Gly Ser Arg Gly Asp Gln Gly Pro Lys Gly Ala
                165                 170                 175

Glu Gly Ala Pro Gly Lys Glu Gly Val Arg Gly Leu Pro Gly Pro Ala
            180                 185                 190

Gly Ala Pro Gly Leu Gln Gly Ala Pro Gly Leu Gln Gly Met Pro Gly
        195                 200                 205

Glu Arg Gly Ala Ala Gly Leu Pro Gly Pro Lys Gly Gln Arg Gly Asp
210                 215                 220

Asn Gly Pro Lys Gly Ala Glu Gly Ala Pro Gly Ala Pro Gly Leu Gln
225                 230                 235                 240

Gly Met Pro Gly Glu Arg Gly Ala Ala Gly Leu Pro Gly Pro Lys Gly
                245                 250                 255

Asn Arg Gly Asp Lys Gly Pro Lys Gly Ala Glu Gly Ala Pro Gly Lys
            260                 265                 270

Glu Gly Val Arg Gly Leu Pro Gly Pro Ile Gly Pro Pro Gly Glu Arg
        275                 280                 285

Gly Ala Ala Gly Leu Pro Gly Pro Lys Gly Asn Arg Gly Asp Glu Gly
290                 295                 300

Pro Lys Gly Ala Glu Gly Ala Pro Gly Lys Glu Gly Val Arg Gly Leu
305                 310                 315                 320

Gln Gly Pro Ile Gly Pro Pro Gly Pro Ala Gly Ala Pro Gly Ala Pro
                325                 330                 335

Gly Leu Gln Gly Met Pro Gly Glu Arg Gly Ala Ala Gly Leu Pro Gly
            340                 345                 350

Pro Lys Gly Ser Arg Gly Asp Gln Gly Pro Lys Gly Ala Glu Gly Ala
        355                 360                 365

Pro Gly Lys Glu Gly Val Arg Gly Leu Pro Gly Pro Ala Gly Ala Pro
370                 375                 380

Gly Leu Gln Gly Ala Pro Gly Leu Gln Gly Met Pro Gly Glu Arg Gly
385                 390                 395                 400

Ala Ala Gly Leu Pro Gly Pro Lys Gly Gln Arg Gly Asp Asn Gly Pro
                405                 410                 415

Lys Gly Ala Glu Gly Ala Pro Gly Ala Pro Gly Leu Gln Gly Met Pro
            420                 425                 430

Gly Glu Arg Gly Ala Ala Gly Leu Pro Gly Lys Gly Asn Arg Gly
        435                 440                 445

Asp Lys Gly Pro Lys Gly Ala Glu Gly Ala Pro Gly Lys Glu Gly Val
        450                 455                 460

Arg Gly Leu Pro Gly Pro Ile Gly Pro Pro Gly Glu Arg Gly Ala Ala
465                 470                 475                 480

Gly Leu Pro Gly Pro Lys Gly Asn Arg Gly Asp Glu Gly Pro Lys Gly
```

```
                    485                 490                 495
Ala Glu Gly Ala Pro Gly Lys Glu Gly Val Arg Gly Leu Gln Gly Pro
                500                 505                 510

Ile Gly Pro Pro Gly Pro Ala Gly Ala Pro Gly Ala Pro Gly Leu Gln
            515                 520                 525

Gly Met Pro Gly Glu Arg Gly Ala Ala Gly Leu Pro Gly Pro Lys Gly
        530                 535                 540

Ser Arg Gly Asp Gln Gly Pro Lys Gly Ala Glu Gly Ala Pro Gly Lys
545                 550                 555                 560

Glu Gly Val Arg Gly Leu Pro Gly Pro Ala Gly Gly
                565                 570

<210> SEQ ID NO 12
<211> LENGTH: 572
<212> TYPE: PRT
<213> ORGANISM: Artificial
<220> FEATURE:
<223> OTHER INFORMATION: Sequence of ICP3 variant 4

<400> SEQUENCE: 12

Gly Pro Pro Gly Ala Pro Gly Leu Gln Gly Ala Pro Gly Leu Gln Gly
1               5                   10                  15

Met Pro Gly Glu Lys Gly Ala Ala Gly Leu Pro Gly Pro Lys Gly Gln
            20                  25                  30

Arg Gly Asp Asn Gly Pro Lys Gly Ala Glu Gly Ala Pro Gly Ala Pro
        35                  40                  45

Gly Leu Gln Gly Met Pro Gly Glu Lys Gly Ala Ala Gly Leu Pro Gly
    50                  55                  60

Pro Lys Gly Asn Arg Gly Asp Lys Gly Pro Lys Gly Ala Glu Gly Ala
65                  70                  75                  80

Pro Gly Lys Glu Gly Val Arg Gly Leu Pro Gly Pro Ile Gly Pro Pro
                85                  90                  95

Gly Glu Lys Gly Ala Ala Gly Leu Pro Gly Pro Lys Gly Asn Arg Gly
            100                 105                 110

Asp Glu Gly Pro Lys Gly Ala Glu Gly Ala Pro Gly Lys Glu Gly Val
        115                 120                 125

Arg Gly Leu Gln Gly Pro Ile Gly Pro Pro Gly Pro Ala Gly Ala Pro
    130                 135                 140

Gly Ala Pro Gly Leu Gln Gly Met Pro Gly Glu Lys Gly Ala Ala Gly
145                 150                 155                 160

Leu Pro Gly Pro Lys Gly Ser Arg Gly Asp Gln Gly Pro Lys Gly Ala
                165                 170                 175

Glu Gly Ala Pro Gly Lys Glu Gly Val Arg Gly Leu Pro Gly Pro Ala
            180                 185                 190

Gly Ala Pro Gly Leu Gln Gly Ala Pro Gly Leu Gln Gly Met Pro Gly
        195                 200                 205

Glu Lys Gly Ala Ala Gly Leu Pro Gly Pro Lys Gly Gln Arg Gly Asp
    210                 215                 220

Asn Gly Pro Lys Gly Ala Glu Gly Ala Pro Gly Ala Pro Gly Leu Gln
225                 230                 235                 240

Gly Met Pro Gly Glu Lys Gly Ala Ala Gly Leu Pro Gly Pro Lys Gly
                245                 250                 255

Asn Arg Gly Asp Lys Gly Pro Lys Gly Ala Glu Gly Ala Pro Gly Lys
            260                 265                 270

Glu Gly Val Arg Gly Leu Pro Gly Pro Ile Gly Pro Pro Gly Glu Lys
```

```
            275                 280                 285
Gly Ala Ala Gly Leu Pro Gly Pro Lys Gly Asn Arg Gly Asp Glu Gly
        290                 295                 300
Pro Lys Gly Ala Glu Gly Ala Pro Gly Lys Glu Gly Val Arg Gly Leu
305                 310                 315                 320
Gln Gly Pro Ile Gly Pro Pro Gly Pro Ala Gly Ala Pro Gly Ala Pro
            325                 330                 335
Gly Leu Gln Gly Met Pro Gly Glu Lys Gly Ala Ala Gly Leu Pro Gly
        340                 345                 350
Pro Lys Gly Ser Arg Gly Asp Gln Gly Pro Lys Gly Ala Glu Gly Ala
            355                 360                 365
Pro Gly Lys Glu Gly Val Arg Gly Leu Pro Gly Pro Ala Gly Ala Pro
        370                 375                 380
Gly Leu Gln Gly Ala Pro Gly Leu Gln Gly Met Pro Gly Glu Lys Gly
385                 390                 395                 400
Ala Ala Gly Leu Pro Gly Pro Lys Gly Gln Arg Gly Asp Asn Gly Pro
            405                 410                 415
Lys Gly Ala Glu Gly Ala Pro Gly Ala Pro Gly Leu Gln Gly Met Pro
        420                 425                 430
Gly Glu Lys Gly Ala Ala Gly Leu Pro Gly Pro Lys Gly Asn Arg Gly
            435                 440                 445
Asp Lys Gly Pro Lys Gly Ala Glu Gly Ala Pro Gly Lys Glu Gly Val
        450                 455                 460
Arg Gly Leu Pro Gly Pro Ile Gly Pro Pro Gly Glu Lys Gly Ala Ala
465                 470                 475                 480
Gly Leu Pro Gly Pro Lys Gly Asn Arg Gly Asp Gly Pro Lys Gly
            485                 490                 495
Ala Glu Gly Ala Pro Gly Lys Glu Gly Val Arg Gly Leu Gln Gly Pro
        500                 505                 510
Ile Gly Pro Pro Gly Pro Ala Gly Ala Pro Gly Ala Pro Gly Leu Gln
            515                 520                 525
Gly Met Pro Gly Glu Lys Gly Ala Ala Gly Leu Pro Gly Pro Lys Gly
        530                 535                 540
Ser Arg Gly Asp Gln Gly Pro Lys Gly Ala Glu Gly Ala Pro Gly Lys
545                 550                 555                 560
Glu Gly Val Arg Gly Leu Pro Gly Pro Ala Gly Gly
            565                 570

<210> SEQ ID NO 13
<211> LENGTH: 545
<212> TYPE: PRT
<213> ORGANISM: Artificial
<220> FEATURE:
<223> OTHER INFORMATION: Sequence of ICP3 variant 6

<400> SEQUENCE: 13

Gly Pro Pro Gly Ala Pro Gly Leu Gln Gly Ala Pro Gly Leu Gln Gly
1               5                   10                  15
Met Pro Gly Glu Arg Gly Ala Ala Gly Leu Pro Gly Pro Lys Gly Glu
            20                  25                  30
Arg Gly Asp Val Gly Pro Lys Gly Ala Glu Gly Ala Pro Gly Ala Pro
        35                  40                  45
Gly Leu Gln Gly Met Pro Gly Glu Arg Gly Ala Ala Gly Leu Pro Gly
    50                  55                  60
Pro Lys Gly Glu Arg Gly Asp Lys Gly Pro Lys Gly Ala Glu Gly Ala
```

```
                 65                  70                  75                  80
Pro Gly Lys Glu Gly Val Arg Gly Pro Ile Gly Pro Pro Gly Glu Arg
                     85                  90                  95
Gly Ala Ala Gly Leu Pro Gly Pro Lys Gly Glu Arg Gly Asp Glu Gly
                    100                 105                 110
Pro Lys Gly Ala Glu Gly Ala Pro Gly Lys Glu Gly Val Arg Gly Pro
                    115                 120                 125
Ile Gly Pro Pro Gly Pro Ala Gly Ala Pro Gly Ala Pro Gly Leu Gln
            130                 135                 140
Gly Met Pro Gly Glu Arg Gly Ala Ala Gly Leu Pro Gly Pro Lys Gly
145                 150                 155                 160
Glu Arg Gly Asp Gln Gly Pro Lys Gly Ala Glu Gly Ala Pro Gly Lys
                    165                 170                 175
Glu Gly Val Arg Gly Pro Ala Gly Ala Pro Gly Leu Gln Gly Ala Pro
                    180                 185                 190
Gly Leu Gln Gly Met Pro Gly Glu Arg Gly Ala Ala Gly Leu Pro Gly
                    195                 200                 205
Pro Lys Gly Glu Arg Gly Asp Val Gly Pro Lys Gly Ala Glu Gly Ala
                    210                 215                 220
Pro Gly Ala Pro Gly Leu Gln Gly Met Pro Gly Glu Arg Gly Ala Ala
225                 230                 235                 240
Gly Leu Pro Gly Pro Lys Gly Glu Arg Gly Asp Lys Gly Pro Lys Gly
                    245                 250                 255
Ala Glu Gly Ala Pro Gly Lys Glu Gly Val Arg Gly Pro Ile Gly Pro
                    260                 265                 270
Pro Gly Glu Arg Gly Ala Ala Gly Leu Pro Gly Pro Lys Gly Glu Arg
                    275                 280                 285
Gly Asp Glu Gly Pro Lys Gly Ala Glu Gly Ala Pro Gly Lys Glu Gly
            290                 295                 300
Val Arg Gly Pro Ile Gly Pro Pro Gly Pro Ala Gly Ala Pro Gly Ala
305                 310                 315                 320
Pro Gly Leu Gln Gly Met Pro Gly Glu Arg Gly Ala Ala Gly Leu Pro
                    325                 330                 335
Gly Pro Lys Gly Glu Arg Gly Asp Gln Gly Pro Lys Gly Ala Glu Gly
                    340                 345                 350
Ala Pro Gly Lys Glu Gly Val Arg Gly Pro Ala Gly Ala Pro Gly Leu
                    355                 360                 365
Gln Gly Ala Pro Gly Leu Gln Gly Met Pro Gly Glu Arg Gly Ala Ala
            370                 375                 380
Gly Leu Pro Gly Pro Lys Gly Glu Arg Gly Asp Val Gly Pro Lys Gly
385                 390                 395                 400
Ala Glu Gly Ala Pro Gly Ala Pro Gly Leu Gln Gly Met Pro Gly Glu
                    405                 410                 415
Arg Gly Ala Ala Gly Leu Pro Gly Pro Lys Gly Glu Arg Gly Asp Lys
                    420                 425                 430
Gly Pro Lys Gly Ala Glu Gly Ala Pro Gly Lys Glu Gly Val Arg Gly
            435                 440                 445
Pro Ile Gly Pro Pro Gly Glu Arg Gly Ala Ala Gly Leu Pro Gly Pro
            450                 455                 460
Lys Gly Glu Arg Gly Asp Glu Gly Pro Lys Gly Ala Glu Gly Ala Pro
465                 470                 475                 480
Gly Lys Glu Gly Val Arg Gly Pro Ile Gly Pro Pro Gly Pro Ala Gly
            485                 490                 495
```

-continued

```
Ala Pro Gly Ala Pro Gly Leu Gln Gly Met Pro Gly Glu Arg Gly Ala
            500                 505                 510

Ala Gly Leu Pro Gly Pro Lys Gly Glu Arg Gly Asp Gln Gly Pro Lys
        515                 520                 525

Gly Ala Glu Gly Ala Pro Gly Lys Glu Gly Val Arg Gly Pro Ala Gly
    530                 535                 540

Gly
545

<210> SEQ ID NO 14
<211> LENGTH: 536
<212> TYPE: PRT
<213> ORGANISM: Artificial
<220> FEATURE:
<223> OTHER INFORMATION: Sequence of ICP3 variant 7

<400> SEQUENCE: 14

Gly Pro Pro Gly Ala Pro Gly Leu Gln Gly Ala Pro Gly Leu Gln Gly
1               5                   10                  15

Met Pro Gly Glu Arg Gly Ala Ala Gly Leu Pro Gly Pro Lys Gly Glu
            20                  25                  30

Val Gly Pro Lys Gly Ala Glu Gly Ala Pro Gly Ala Pro Gly Leu Gln
        35                  40                  45

Gly Met Pro Gly Glu Arg Gly Ala Ala Gly Leu Pro Gly Pro Lys Gly
    50                  55                  60

Glu Lys Gly Pro Lys Gly Ala Glu Gly Ala Pro Gly Lys Glu Gly Val
65                  70                  75                  80

Arg Gly Leu Ala Gly Pro Ile Gly Pro Pro Gly Glu Arg Gly Ala Ala
                85                  90                  95

Gly Leu Pro Gly Pro Lys Gly Glu Glu Gly Pro Lys Gly Ala Glu Gly
            100                 105                 110

Ala Pro Gly Lys Glu Gly Val Arg Gly Leu Ala Gly Pro Ile Gly Pro
        115                 120                 125

Pro Gly Pro Ala Gly Ala Pro Gly Ala Pro Gly Leu Gln Gly Met Pro
    130                 135                 140

Gly Glu Arg Gly Ala Ala Gly Leu Pro Gly Pro Lys Gly Glu Gln Gly
145                 150                 155                 160

Pro Lys Gly Ala Glu Gly Ala Pro Gly Lys Glu Gly Val Arg Gly Leu
                165                 170                 175

Ala Gly Pro Ala Gly Ala Pro Gly Leu Gln Gly Ala Pro Gly Leu Gln
            180                 185                 190

Gly Met Pro Gly Glu Arg Gly Ala Ala Gly Leu Pro Gly Pro Lys Gly
        195                 200                 205

Glu Val Gly Pro Lys Gly Ala Glu Gly Ala Pro Gly Ala Pro Gly Leu
    210                 215                 220

Gln Gly Met Pro Gly Glu Arg Gly Ala Ala Gly Leu Pro Gly Pro Lys
225                 230                 235                 240

Gly Glu Lys Gly Pro Lys Gly Ala Glu Gly Ala Pro Gly Lys Glu Gly
                245                 250                 255

Val Arg Gly Leu Ala Gly Pro Ile Gly Pro Pro Gly Glu Arg Gly Ala
            260                 265                 270

Ala Gly Leu Pro Gly Pro Lys Gly Glu Glu Gly Pro Lys Gly Ala Glu
        275                 280                 285

Gly Ala Pro Gly Lys Glu Gly Val Arg Gly Leu Ala Gly Pro Ile Gly
    290                 295                 300
```

-continued

Pro Pro Gly Pro Ala Gly Ala Pro Gly Ala Pro Gly Leu Gln Gly Met
305                 310                 315                 320

Pro Gly Glu Arg Gly Ala Ala Gly Leu Pro Gly Pro Lys Gly Glu Gln
            325                 330                 335

Gly Pro Lys Gly Ala Glu Gly Ala Pro Gly Lys Glu Gly Val Arg Gly
            340                 345                 350

Leu Ala Gly Pro Ala Gly Ala Pro Gly Leu Gln Gly Ala Pro Gly Leu
            355                 360                 365

Gln Gly Met Pro Gly Glu Arg Gly Ala Ala Gly Leu Pro Gly Pro Lys
370                 375                 380

Gly Glu Val Gly Pro Lys Gly Ala Glu Gly Ala Pro Gly Ala Pro Gly
385                 390                 395                 400

Leu Gln Gly Met Pro Gly Glu Arg Gly Ala Ala Gly Leu Pro Gly Pro
            405                 410                 415

Lys Gly Glu Lys Gly Pro Lys Gly Ala Glu Gly Ala Pro Gly Lys Glu
            420                 425                 430

Gly Val Arg Gly Leu Ala Gly Pro Ile Gly Pro Pro Gly Glu Arg Gly
            435                 440                 445

Ala Ala Gly Leu Pro Gly Pro Lys Gly Glu Glu Gly Pro Lys Gly Ala
450                 455                 460

Glu Gly Ala Pro Gly Lys Glu Gly Val Arg Gly Leu Ala Gly Pro Ile
465                 470                 475                 480

Gly Pro Pro Gly Pro Ala Gly Ala Pro Gly Ala Pro Gly Leu Gln Gly
            485                 490                 495

Met Pro Gly Glu Arg Gly Ala Ala Gly Leu Pro Gly Pro Lys Gly Glu
            500                 505                 510

Gln Gly Pro Lys Gly Ala Glu Gly Ala Pro Gly Lys Glu Gly Val Arg
            515                 520                 525

Gly Leu Ala Gly Pro Ala Gly Gly
            530                 535

<210> SEQ ID NO 15
<211> LENGTH: 545
<212> TYPE: PRT
<213> ORGANISM: Artificial
<220> FEATURE:
<223> OTHER INFORMATION: Sequence of ICP variant 8

<400> SEQUENCE: 15

Gly Pro Pro Gly Ala Pro Gly Leu Gln Gly Ala Pro Gly Leu Gln Gly
1               5                   10                  15

Met Pro Gly Glu Arg Gly Ala Pro Gly Leu Pro Gly Pro Lys Gly Glu
            20                  25                  30

Arg Gly Asp Val Gly Pro Lys Gly Ala Glu Gly Ala Pro Gly Ala Pro
            35                  40                  45

Gly Leu Gln Gly Met Pro Gly Glu Arg Gly Ala Pro Gly Leu Pro Gly
        50                  55                  60

Pro Lys Gly Glu Arg Gly Asp Lys Gly Pro Lys Gly Ala Glu Gly Ala
65                  70                  75                  80

Pro Gly Lys Glu Gly Val Arg Gly Pro Ile Gly Pro Pro Gly Glu Arg
            85                  90                  95

Gly Ala Pro Gly Leu Pro Gly Pro Lys Gly Glu Arg Gly Asp Glu Gly
            100                 105                 110

Pro Lys Gly Ala Glu Gly Ala Pro Gly Lys Glu Gly Val Arg Gly Pro
            115                 120                 125

```
Ile Gly Pro Pro Gly Ala Gly Ala Pro Gly Ala Pro Gly Leu Gln
    130                 135                 140

Gly Met Pro Gly Glu Arg Gly Ala Pro Gly Leu Pro Gly Pro Lys Gly
145                 150                 155                 160

Glu Arg Gly Asp Gln Gly Pro Lys Gly Ala Glu Gly Ala Pro Gly Lys
                165                 170                 175

Glu Gly Val Arg Gly Pro Ala Gly Ala Pro Gly Leu Gln Gly Ala Pro
            180                 185                 190

Gly Leu Gln Gly Met Pro Gly Glu Arg Gly Ala Pro Gly Leu Pro Gly
        195                 200                 205

Pro Lys Gly Glu Arg Gly Asp Val Gly Pro Lys Gly Ala Glu Gly Ala
    210                 215                 220

Pro Gly Ala Pro Gly Leu Gln Gly Met Pro Gly Glu Arg Gly Ala Pro
225                 230                 235                 240

Gly Leu Pro Gly Pro Lys Gly Glu Arg Gly Asp Lys Gly Pro Lys Gly
                245                 250                 255

Ala Glu Gly Ala Pro Gly Lys Glu Gly Val Arg Gly Pro Ile Gly Pro
            260                 265                 270

Pro Gly Glu Arg Gly Ala Pro Gly Leu Pro Gly Pro Lys Gly Glu Arg
        275                 280                 285

Gly Asp Glu Gly Pro Lys Gly Ala Glu Gly Ala Pro Gly Lys Glu Gly
    290                 295                 300

Val Arg Gly Pro Ile Gly Pro Pro Gly Pro Ala Gly Ala Pro Gly Ala
305                 310                 315                 320

Pro Gly Leu Gln Gly Met Pro Gly Glu Arg Gly Ala Pro Gly Leu Pro
                325                 330                 335

Gly Pro Lys Gly Glu Arg Gly Asp Gln Gly Pro Lys Gly Ala Glu Gly
            340                 345                 350

Ala Pro Gly Lys Glu Gly Val Arg Gly Pro Ala Gly Ala Pro Gly Leu
        355                 360                 365

Gln Gly Ala Pro Gly Leu Gln Gly Met Pro Gly Glu Arg Gly Ala Pro
    370                 375                 380

Gly Leu Pro Gly Pro Lys Gly Glu Arg Gly Asp Val Gly Pro Lys Gly
385                 390                 395                 400

Ala Glu Gly Ala Pro Gly Ala Pro Gly Leu Gln Gly Met Pro Gly Glu
                405                 410                 415

Arg Gly Ala Pro Gly Leu Pro Gly Pro Lys Gly Glu Arg Gly Asp Lys
            420                 425                 430

Gly Pro Lys Gly Ala Glu Gly Ala Pro Gly Lys Glu Gly Val Arg Gly
        435                 440                 445

Pro Ile Gly Pro Pro Gly Glu Arg Gly Ala Pro Gly Leu Pro Gly Pro
    450                 455                 460

Lys Gly Glu Arg Gly Asp Glu Gly Pro Lys Gly Ala Glu Gly Ala Pro
465                 470                 475                 480

Gly Lys Glu Gly Val Arg Gly Pro Ile Gly Pro Pro Gly Pro Ala Gly
                485                 490                 495

Ala Pro Gly Ala Pro Gly Leu Gln Gly Met Pro Gly Glu Arg Gly Ala
            500                 505                 510

Pro Gly Leu Pro Gly Pro Lys Gly Glu Arg Gly Asp Gln Gly Pro Lys
        515                 520                 525
```

```
Gly Ala Glu Gly Ala Pro Gly Lys Glu Gly Val Arg Gly Pro Ala Gly
    530                 535                 540
Gly
545
```